(12) United States Patent
Foley et al.

(10) Patent No.: US 6,900,893 B2
(45) Date of Patent: May 31, 2005

(54) OPTICAL PATH STRUCTURE FOR OPEN PATH EMISSIONS SENSING WITH PARTICULATE MATTER AND LUBRICATING OIL CONSUMPTION ABSORPTION METHODOLOGY

(75) Inventors: Theresa A. Foley, Delevan, WI (US); John DiDomenico, Tucson, AZ (US); Robert A. Gentala, Tucson, AZ (US); Craig S. Rendahl, Tucson, AZ (US)

(73) Assignee: SPX Corporation, Charlotte, NC (US)

( * ) Notice: Subject to any disclaimer, the term of this patent is extended or adjusted under 35 U.S.C. 154(b) by 124 days.

(21) Appl. No.: 10/142,061

(22) Filed: May 10, 2002

(65) Prior Publication Data

US 2003/0058451 A1 Mar. 27, 2003

Related U.S. Application Data

(63) Continuation-in-part of application No. 09/934,272, filed on Aug. 21, 2001, now Pat. No. 6,744,516.

(51) Int. Cl.⁷ .......................... G01N 21/00; G01J 5/00
(52) U.S. Cl. .............. 356/437; 250/339.01; 250/339.05
(58) Field of Search ................................. 356/432–440, 356/335–343; 250/339.01, 339.05, 338.1, 338.5, 336.1, 339.13, 372, 339.11, 343, 345; 73/1.06

(56) References Cited

U.S. PATENT DOCUMENTS

| | | | |
|---|---|---|---|
| 3,628,028 A | * 12/1971 | Thorsheim | 250/576 |
| 3,696,247 A | 10/1972 | McIntosh et al. | 250/83.3 H |
| 3,811,776 A | 5/1974 | Blau, Jr. | 356/51 |
| 3,957,372 A | 5/1976 | Jowett et al. | 356/51 |
| 3,958,122 A | 5/1976 | Jowett et al. | 250/346 |
| 3,973,848 A | 8/1976 | Jowett et al. | 356/51 |
| 4,012,144 A | 3/1977 | Hedelman | 356/73 |
| 4,013,260 A | 3/1977 | McClatchie et al. | 250/343 |
| 4,160,373 A | 7/1979 | Fastaia et al. | 73/23 |
| 4,171,909 A | 10/1979 | Kramer et al. | 356/73 |
| 4,204,768 A | 5/1980 | N'Guyen | 356/243 |
| 4,310,249 A | 1/1982 | Kramer | 356/414 |
| 4,348,732 A | 9/1982 | Kreft | 364/571 |
| 4,372,155 A | 2/1983 | Butler et al. | 73/114 |
| 4,390,785 A | 6/1983 | Faulhaber et al. | 250/330 |
| 4,432,316 A | 2/1984 | Ogita | 123/328 |
| 4,490,845 A | 12/1984 | Steinbruegge et al. | 382/1 |
| 4,560,873 A | 12/1985 | McGowan et al. | 250/339 |
| 4,602,160 A | 7/1986 | Mactaggart | 250/341 |
| 4,632,563 A | 12/1986 | Lord, III | 356/437 |
| 4,638,345 A | 1/1987 | Elabd et al. | 357/24 |
| 4,663,522 A | 5/1987 | Welbourn et al. | 250/223 R |
| 4,678,914 A | 7/1987 | Melrose et al. | 250/343 |
| 4,687,934 A | 8/1987 | Passaro et al. | 250/343 |
| 4,710,630 A | 12/1987 | Kuppenheimer, Jr. et al. | 250/353 |

(Continued)

OTHER PUBLICATIONS

Radian Corp.; "Developing an Inspection/Maintenance Program for Alternatively–Fueled Vehicles"; 1993.

Islam, Muhammed, Rendahl, Craig S., Cors, Rebecca; "Wisconsin's Remove Vehicle Emissions Sensing Study"; Final Report 1995.

Walsh, P.A., Gertler, A.W.; "Texas 1996 Remote Sensing Feasibility Study"; Final Report 1997.

(Continued)

*Primary Examiner*—Hoa Q. Pham
(74) *Attorney, Agent, or Firm*—Baker & Hostetler LLP

(57) ABSTRACT

A device for measuring particulate matter includes a light source that emits light, a receiver positioned to receive light emitted from the light source, and a detection unit in communication with the receiver. The detection unit detects an amount of particulate matter based upon the light received by the receiver.

17 Claims, 14 Drawing Sheets

U.S. PATENT DOCUMENTS

| | | | |
|---|---|---|---|
| 4,746,218 A | 5/1988 | Lord, III | 356/437 |
| 4,795,253 A | 1/1989 | Sandridge et al. | 356/51 |
| 4,818,705 A | 4/1989 | Schneider et al. | 436/164 |
| 4,829,183 A | 5/1989 | McClatchie et al. | 250/346 |
| 4,868,622 A | 9/1989 | Shigenaka | 357/30 |
| 4,875,084 A | 10/1989 | Tohyama | 357/30 |
| 4,914,719 A | 4/1990 | Conlon et al. | 250/339 |
| 4,924,095 A | 5/1990 | Swanson, Jr. | 250/338.5 |
| 4,963,023 A | 10/1990 | Goldovsky et al. | 356/308 |
| 4,999,498 A | 3/1991 | Hunt et al. | 250/338.5 |
| 5,002,391 A | 3/1991 | Wolfrum et al. | 356/307 |
| 5,009,064 A * | 4/1991 | Grob et al. | 60/276 |
| 5,041,723 A | 8/1991 | Ishida et al. | 250/339 |
| 5,061,854 A | 10/1991 | Kroutil et al. | 250/339 |
| 5,076,699 A | 12/1991 | Ryan et al. | 356/437 |
| 5,157,288 A | 10/1992 | Hill | 307/511 |
| 5,185,648 A | 2/1993 | Baker et al. | 257/189 |
| 5,210,702 A | 5/1993 | Bishop et al. | 364/496 |
| 5,239,860 A | 8/1993 | Harris et al. | 73/61.48 |
| 5,252,828 A | 10/1993 | Kert et al. | 250/339 |
| 5,255,511 A | 10/1993 | Maus et al. | 60/274 |
| 5,307,626 A | 5/1994 | Maus et al. | 60/274 |
| 5,319,199 A | 6/1994 | Stedman et al. | 250/338.5 |
| 5,332,901 A | 7/1994 | Eckles et al. | 250/345 |
| 5,343,043 A | 8/1994 | Johnson | 250/338.5 |
| 5,361,171 A | 11/1994 | Bleier | 359/855 |
| 5,371,367 A | 12/1994 | DiDomenico et al. | 250/338.5 |
| 5,373,160 A | 12/1994 | Taylor | 250/338.5 |
| 5,401,967 A | 3/1995 | Stedman et al. | 250/338.5 |
| 5,418,366 A | 5/1995 | Rubin et al. | 250/338.5 |
| 5,489,777 A | 2/1996 | Stedman et al. | 250/338.5 |
| 5,498,872 A | 3/1996 | Stedman et al. | 250/338.5 |
| 5,545,897 A | 8/1996 | Jack | 250/339.13 |
| 5,583,765 A | 12/1996 | Kleehammer | 364/423.098 |
| 5,591,975 A | 1/1997 | Jack et al. | 250/338.5 |
| 5,621,166 A | 4/1997 | Butler | 73/116 |
| 5,644,133 A | 7/1997 | Didomenico et al. | 250/338.5 |
| 5,719,396 A | 2/1998 | Jack et al. | 250/338.5 |
| 5,726,450 A | 3/1998 | Peterson et al. | 250/338.5 |
| 5,797,682 A | 8/1998 | Kert et al. | 374/123 |
| 5,812,249 A | 9/1998 | Johnson et al. | 356/28 |
| 5,831,267 A | 11/1998 | Jack et al. | 250/338.5 |
| 5,922,948 A | 7/1999 | Lesko et al. | 73/117.3 |
| 6,057,923 A | 5/2000 | Sachse | 356/364 |
| 6,230,087 B1 | 5/2001 | Didomenico et al. | 701/29 |
| 6,307,201 B1 | 10/2001 | Didomenico et al. | 250/339.13 |
| 6,723,990 B2 * | 4/2004 | DiDomenico et al. | 250/339.05 |
| 6,744,516 B2 * | 6/2004 | DiDomenico et al. | 356/437 |

OTHER PUBLICATIONS

Popp, Peter J.; "Development of High–Speed Ultraviolet Spectrophotometer Capable of Real–Time NO and Aromatic Hydrocarbon Detection in Vehicle Exhaust"; pp. 4–3 & 4–12;Coordinating Research Council 1997.

McVey, Iain Frederick; "Development of a Remote Sensor for Mobile Source Nitric Oxide"; University of Denver 1992.

Beaton, S.P., Bishop, G.A. and Stedman D.H.; Emissions Characteristics of Mexico City Vehicles; pp. 42, 1424–1429; Journal of Air and Waste Management Assoc. 1992.

Zhang, Yi, Stedman, Donald H., Bishop, Gary A., Beaton, Stuart P., Guenther, Paul L. and McVey, Iain F.; "Enhancement of Remote Sensing for Mobile Source Nitric Oxide"; Journal of Air & Waste Management 1996; vol. 46, pp. 25–29.

Popp, Peter John; "Remote Sensing of Nitric Oxide Emissions from Planes, Trains and Automobiles"; University of Denver 1999.

Zhang, Yi, Stedman, Donald H., Bishop, Gary A., Beaton, Stuart P., and Guenther, Paul L.; "Worldwide On–Road Vehicle Exhaust Emissions Study by Remote Sensing"; Environmental Science & Technology 1995; vol. 29#9. Pp. 2286–2294.

Glover, Edward L., Mickelsen, Jan and McClement Dennis; Evaluation of Methods to Determine Catalyst Efficiency in the Inspection/Maintenance Process; Society of Automotive Engineers; SAE#9600092.

Butler, James, Gierczak, Christine and Liscombe Paula; "Factors Affecting the NDIR Measurement of Exhaust Hydrocarbons"; Coordinating Research Council 1995; pp. 4–171 & 4–190.

MacKay, Gervase I. Nadler, S. Don, Karecki, David R., Schiff, Harold I., Butler, James W., Gierczak, Christine A. and Jesion, Gerald; "Final Phase 1b Report to the CRC and NREL for Research Performed Under Agreement No. VE–8–2"; Coordinating Research Council 1994.

Peterson, James E. and Stedman, Donald H.; "Find and Fix the Polluters"; Chemtech 1992; pp. 47–53.

Bishop, Gary A. and Stedman Donald H.; "Infrared Emissions and Remote Sensing"; Journal of Air and Waste Management Assoc. 1992; vol. 42#5, pp. 695–697.

Bishop, Gary A., Starkey, John R., Ihlenfeldt, Anne, Williams, Walter J. and Stedman Donald H.; "IR Long–Path Photometry: A Remote Sensing Tool for Automobile Emissions"; Analytical Chemistry 1989; vol. 61#10, pp. 671A–677A.

Axelsson, Hakan, Eilard, Anders, Emanuelsson, Annika, Galle, Bo, Edner, Hans, Regnarson Par and Kloo Henrik; "Measurement of Aromatic Hydrocarbons with the DOAS Technique"; Applied Spectroscopy 1995; vol. 49#9, pp. 1254–1260.

Baum, Marc M., Kiyomiya, Eileen S., Kumar Sasi and Lappas, Anastasios M. ' "Multicomponent Remote Sensing of Vehicle Exhaust by Dispersive Absorption Spectroscopy. 1. Effect of Fuel Type and Catalyst Performance"; Environmental Science and Technology 2000; pp. 34 & 2851–2858.

Stedman, David H. and Smith, Dennis L.; "$NO_x$ Data by Remote Sensing"; Coordinating Research Council 1995; pp. 4–47 & 4–63.

Shore, P.R. and Devries, R.S.; "On–line Hydrocarbon Speciation Using FTIR and CI–MS"; Society of Automotive Engineers 1992; SAE #922246.

Bishop, Gary A. and Stedman, Donald H.; "On–Road Carbon Monoxide Emission Measurement Comparisons for the 1988–1989 Colorado Oxy–Fuels Program"; Environmental Science & Technology 1990; pp. 24 & 843–847.

Stedman, Donald H., Bishop, Gary, Peterson, James E., and Geunther, Paul L.; "On–Road CO Remote Sensing in the Los Angeles Basin"; CA–EPA (CARB) 1991; pp. 24 & 843–847.

X–Rite Incorporated; "A Guide to Integrating Sphere Theory and Applications"; 2002; www.labsphere.com.

Geunther, Paul L., Stedman, Donald H., Bishop, Gary A., Beaton, Stuaret P., Bean, James H. and Quine Richard W.; "A Hydrocarbon Detector for the Remote Sensing of Vehicle Exhaust Emissions"; Review of Scientific Instruments 1994; vol. 66(4), pp. 3024–3029.

Stephens, Robert D., Mulawa, Patricia A., Giles, Michael T., Kennedy, Kenneth G., Groblicki, Peter J. and Cadle, Steven H.; "An Experimental Evaluation of Remote Sensing–Based Hydrocarbon Measurements: A Comparison to FID Measurements"; Journal of Air and Waste Management Assoc. 1996; pp. 46 & 148–158.

Stedman, Donald H.; "Automobile Carbon Monoxide Emissions"; Environmental Science and Technology 1989; vol. 23#2, pp. 147–149.

Adachi, Masayuki, Yamagishi, Yutaka, Inoue Kaori and Ishida, Kozo; "Automotive Emissions Analyses using FTIR Spectrophotometer"; Society of Automotive Engineers 1992; SAE #920723.

Koplow, Michael D., Jimenez, Jose L., Nelson, David D., Schmidt, Stephan E.; "Characterization of On–Road Vehicle NO Emissions by Means of a TILDAS Remote Sensing Instrument"; Coordinating Research Council 1997; pp. 8–35 & 8–62.

Guenther, Paul Leonard; "Contributions to On–Road Remoter Sensing of Automobile Exhaust"; University of Denver 1992.

Cox, Frank W., Walls, John R. and Carrel, Mark W.; "Determination of Catalyst Oxidation and Reduction Efficiencies from Tailpipe Emissions Measurements"; Society of Automotive Engineers 1997; SAE #972911.

Lawson, Douglas R., Groblicki, Peter J., Stedman, Donald H., Bishop, Gary A. and Guenther Paul L.; "Emissions from In–Use Motor Vehicles in Los Angeles: A Pilot Study of Remote Sensing and the Inspection and Maintenance Program"; Journal of Air and Waste Management Assoc. 1990; vol. 40#8, pp. 1096–1105.

Stedman, Donald H., Bishop, Gary A. and Pitchford, Marc L., "Evaluation of a Remote Sensor for Mobile Source CO Emissions"; University of Denver 1991; Rpt.# EPA 600/4–90/032.

McLaren, Scott E., Stedman, Donald H., Greenlaw, Pamela D., Bath, Raymond J., and Spear, Richard D.; "Comparison of an Open Path UV and FTIR Spectrometer"; Air and Waste Management Assoc. 1992; vol. 92–73.10.

Bishop, Gary A., Zhang, Yi, McLaren, Scott E., Guenther, Paul L., Beaton, James E., Stedman, Donald H., Duncan, John W., McArver, Alexander Q., Pierson, William R., Groblicki, Peter J., Knapp, Kenneth T., Zweidinger, Roy B. and Day, Frank J.; Enhancements of Remote Sensing for Vehicle Emissions in Tunnels; Journal of Air and Waste Management 1994; vol. 44, pp. 169–175.

McLaren, Scott E. and Stedman Donald H.; "Flux Measurements Using Simultaneous Long Path Ultraviolet and Infrared Spectroscopy"; Air and Waste Management Assoc. 1990; vol. 90–86.6.

Bishop, Gary A., McLaren, Scott E., Stedman, Donald H., Pierson, William R., Zweidinger, Roy B. and Ray, William D; "Method Comparisons of Vehicle Emissions Measurements in the Fort McHenry and Tuscarora Mountain Tunnels"; Atmospheric Environment 1996; vol. 30#12, pp. 2307–2316.

McLaren, Scott; "Open Path Spectrometers for Atmospheric Monitoring"; University of Denver 1995.

Stedman, Donald H. and Bishop, Gary A.; "An Analysis of On–Road Remote Sensing as a Tool for Automobile Emissions Control"; Illinois Dept. of Energy & Natural Resources 1990; ILENR/RE–AQ–90/05.

Stedman, Donald H., Peterson, James E. and McVey, Iain F.; "On–Road Carbon Monoxide and Hydrocarbon Remote Sensing in the Chicago Area"; Illinois Dept. of Energy & Natural Resources 1991; ILENR/RE–AQ–91/14.

Lyons, Carol E. and Stedman, Donald H.; "Remote Sensing Enhanced Motor Vehicle Emissions Control for Pollution Reduction in the Chicago Metropolitan Area: Siting and Issue Analysis"; Illinois Dept. of Energy & Natural Resources 1991; ILENR/RE–AQ–91/15.

Durbin, Thomas D., Truex, Timothy J. and Norbeck, Joseph M.; "Particulate Measurements and Emissions Characterizations of Alternative Fuel Vehicle Exhaust"; National Renewable Energy Laboratory 1998; NREL/SR–540–25741; Subcont# ACI–7–16637–01.

Didomenico, John, Johnson, Jim, Webster, Jason and Rendahl, Craig S.; "Preliminary Results from Cold Start Sensor Testing"; Coordinating Research Council 1997; pp. 4–71 & 4–72.

Stephens, Robert D. and Cadle, Steven H.; "Remote Sensing Measurements of Carbon Monoxide Emissions from On–Road Vehicles"; Journal of Air and Waste Management Assoc. 1991; vol. 41#1, pp. 39–46.

Jimenez, Jose L., McRae, Gregory J., Nelson, David D., Zahniser, Mark S. and Kolb, Charles E.; "Remote Sensing of NO and $NO_2$ Emissions from Heavy–Duty Diesel Trucks Using Tunable Diode Lasers"; Environmental Science & Technology 2000; pp. 34 & 2380–2387.

Stedman, Donald H., Bishop, Gary A., Guenther, Paul L., Peterson, James E., Beaton, Stuart P. and McVey Iain F.; "Remote Sensing of On–Road Vehicle Emissions"; University of Denver 1992; Contract #VE–8–1.

Singer, Brett C., Harley, Robert A., Littlejohn, David, Ho, Jerry and Vo, Thu; "Scaling of Infrared Remote Sensor Hydrocarbon Measurements for Motor Vehicle Emission Inventory Calculations"; Environmental Science and Technology 1998; vol. 32#21, pp. 3241–3428.

Atkinson, Chris M., McKain, David L., Gautam, Mridul, El–Gazzar, Laila, Lyons, Donald W. and Clark, Nigel N.; "Speciation of Heavy Duty Diesel Engine Exhaust Emissions"; Coordinating Research Council 1995; pp. 5–71 & 5–92.

Chaney, Lucian W.; "The Remote Measurement of Traffic Generated Carbon Monoxide"; Journal of Air Pollution Control Assoc. 1983; vol. 33#3, pp. 220–222.

Todd, Michael and Barth, Michael; "The Variation of Remote Sensing Emission Measurements with Respect to Vehicle Speed and Acceleration"; Coordinating Research Council 1995; pp. 4–1 & 4–14.

Hoshizaki, H., Wood, A.D and Kemp, D.D.; "Vehicle Inspection Instrumentation"; Lockheed Missiles & Space Company 1973; ARB–3C–235–7.

Sigsby, Jr., John E., Tejada, Silvestre and Ray, William; "Volatile Organic Compound Emissions from 46 In–Use Passenger Cars"; Environmental Science & Technology 1987; pp. 21 & 466–475.

* cited by examiner

OPTICAL PATH STRUCTURE FOR OPEN PATH EMISSIONS SENSING WITH PARTICULATE MATTER AND LUBRICATING OIL CONSUMPTION ABSORPTION METHODOLOGY

PRIORITY

The present application is a continuation-in-part of U.S. patent application Ser. No. 09/934,272, filed Aug. 21, 2001 now U.S. Pat. No. 6,744,516, entitled Optical Path Structure for Open Emissions Sensing, the disclosure of which is incorporated herein by reference in its entirety.

FIELD OF THE INVENTION

The present invention relates generally to remote sensing systems. More particularly, the present invention relates to an apparatus for transmitting, reflecting, and detecting light in an open path sensing system such as a vehicle emission sensing system, having use in detecting and/or measuring one or more components of the air through which the light passes.

BACKGROUND OF THE INVENTION

Current methods of determining whether a vehicle is compliant with emission standards include open path and closed path emissions measurement systems. In a closed path system, an emission sensor is directly connected to the exhaust of the vehicle, such as by insertion into a tailpipe. An open path vehicular emissions measurement system collects data by a means other than a direct connection to the tailpipe, such as a remote sensor that analyzes the individual components of emissions. Open path vehicle emission systems are often preferable to closed path systems because they can be used in numerous locations and do not require the vehicle to stop for testing.

Various open path emission sensing systems have been known. One such device uses a radiation source on one side of a roadway that projects a beam across the roadway to be received by a detector. The radiation source and the detector are located on opposite sides of the roadway. The radiation source emits light spectra that may be used to detect an emission signature by way of absorption of light, or which alternatively may be used to excite emission components so as to cause the components to emit light. The detected emission signature can then be used in various applications, such as the measurement of a vehicle's compliance with emission limits and the determination of the type of fuel that a vehicle is using.

A disadvantage of many known arrangements is that the radiation sources and detectors must be placed on opposite sides of the roadway from each other. Since both the detectors and radiation sources require power to operate, this means that a separate power supply must be provided on each side of the roadway. Some known arrangements have tried to overcome this problem by using a radiation source on one side of a roadway and a reflective apparatus on the other side of the roadway.

Furthermore, current open path embodiments are unable to measure particulate matter (PM), as they are equipped to only measure the density, referred to as "opacity", of smoke emanating from a vehicle's exhaust. Particulate matter is defined to be small solid masses, and include a size of the particle in the symbol for PM. $PM_{10}$ consists of particles with an aerodynamic diameter of 10 microns or less. $PM_{2.5}$ consists of particulate matter with an aerodynamic diameter of 2.5 microns or less. Particles less than 1 micron in diameter tend to lodge deep within the lungs, where the fine particles can cause respiratory or heart problems. $PM_{2.5}$ also impairs visibility. A measurement of opacity historically has not correlated well with actual PM measurements, nor have opacity measurements properly characterized the particle sizes that most affect human health and welfare.

At lease 90% of exhaust particles from gasoline- or diesel-powered vehicles are in the $PM_{2.5}$ size range. Furthermore, most exhaust particles from these fuels are 0.1 to 0.2 micron or smaller. Exhaust particles consist of unburned fuel, motor oil, and partially burned fuel, known as organic carbon (OC), coated onto soot particles that are known as elemental carbon (EC). For diesel exhaust, elemental carbon comprises about 70% of the total PM mass.

The United States Federal Reference Method (40 CFR 86, Subpart N) for sampling particulate matter requires a vehicle to be connected to a dilution tunnel. The exhaust is transported through an insulated, smooth-walled stainless-steel tube to a constant flow dilution tunnel typically operating at 10–30 cubic meters of flow volume per minute at between 20–30° C. The dilution air flow must be sufficient to prevent water condensation, maintain a diluted exhaust temperature at less than 52° C., and ensure turbulent flow. The exhaust is pumped through a filter that is weighed prior to usage for the emissions test. The filter is weighed after the test and the difference in weight prior to and after the emissions test is the PM mass. Using this method, a laboratory must equilibrate the filters for a long period of time in a constant humidity chamber before weighing them.

Other current art, such as a Tapered Element Oscillating Microbalance (TEOM) system, also requires at least a portion of vehicle exhaust to be channeled through a chamber where the amount and size of particulates of exhaust can be analyzed. The TEOM methodology obviates any filter media, assuming that speciation of the particulates is not desired. Nonetheless, the TEOM methodology requires a vehicle to be taken to a specific testing facility, due to the closed-path nature of its methodology, and requires special plumbing modifications if particulates are to be speciated from filter media.

Studies have found that the current closed path embodiments are accurate for measuring total PM mass but overestimate the number of very small exhaust particles (10–30 nanometers) by a factor of two to four. There are two reasons for the very small particle bias. The particulate matter tends to accumulate on the inside of the hose leading from the vehicle tailpipe to the dilution tunnel, causing very small particles to be released during subsequent tests. And the dilution factor of the dilution tunnel is less than would occur under ambient conditions, which can cause gases such as sulfur dioxide to condense into particles. An open path emissions testing embodiment would not suffer the effects of particulates being scavenged in the testing apparatus itself Furthermore, current open path sampling art for measuring opacity does not have a good correlation with the Society of Automotive Engineers (SAE) Snap-Acceleration Smoke Test Procedure issued in SAE bulletin J1667. While this SAE J1667 test is for stationary vehicles on a treadmill, it is nonetheless desirable to have a better method for open path emissions sensors to be able to measure and estimate the opacity of a vehicle's exhaust that has improved correlation with the SAE J1667 standard.

Also, current open path emissions sampling art cannot determine if a tested vehicle was burning excessive amounts of lubricating oil from its engine, due to wear of internal sealing components within the engine or other reason. It is desirable to have a system that can determine whether this excessive lubricating oil burning condition is occurring with each tested vehicle.

Accordingly, it is desirable to provide an improved optical transmission, reflection, and detection system that can additionally measure particulate matter along with gaseous emissions measurements, along with an improved correlation opacity measurement as herein disclosed.

SUMMARY OF THE INVENTION

It is therefore a feature and advantage of the present invention to provide an improved optical transmission, reflection and detection system. In accordance with one embodiment of the present invention, a device for measuring particulate matter includes a light source that emits light, a receiver positioned to receive light emitted from the light source, and a detection unit in communication with the receiver. The detection unit detects an amount of particulate matter based upon the light received by the receiver.

In an alternate embodiment, a method for determining a concentration of particulate matter includes the steps of emitting light from a light source, receiving the light emitted from the light source in a receiver, and determining an amount of particulate matter using the light received in the receiver.

In accordance with another embodiment, a system for measuring particulate matter includes a light source means for emitting light and a receiver means for receiving the light emitted from the light source means. The receiver means is positioned to receive the light emitted from the light source means. The system further includes a detection unit means for determining an amount of particulate matter based upon the light received by the receiver. The detection unit means is in communication with the receiver means.

There have thus been outlined, rather broadly, the more important features of the invention in order that the detailed description thereof that follows may be better understood, and in order that the present contribution to the art may be better appreciated. There are, of course, additional features of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF PREFERRED EMBODIMENTS OF THE INVENTION

A preferred embodiment of the present invention provides an improved optical source, reflection, and detection system for gas component analysis. A preferred embodiment includes a light source unit, which preferably includes one or more of infrared, visible, and ultraviolet light sources; a reflection unit; and a light detection unit. Preferably, light sources and detectors are contained within a housing. The light is transmitted through a gas, such as air containing vehicle emissions, reflected, and detected for analysis and measurement of the amount of absorption that has occurred at known wavelengths of the light. The amount of absorption may be used to determine concentrations of gases corresponding to the specific wavelengths.

In a preferred embodiment of this invention, infrared, visible, and ultraviolet radiation is combined into one beam, directed across a path such as a road along which vehicles travel and generate exhaust, reflected back across the path, collected and concentrated, separated again, and received by one or more discrete detectors and/or spectrometers. In order to be able to separately analyze each range of wavelengths, the infrared light passes through a sequence of filters and/or gas cells either before or after traversing the path of light across the road. The filters are preferably narrow band pass filters and the gas cells contain known concentrations of gases of interest, such that each filter or combination of filters and gas cells is specific to a gas of interest. In one embodiment, a spinning wheel holds the filters and passes each filter in front of the infrared light source in sequence, before the light traverses the road. In an alternate embodiment, the infrared light, after traversing the road, is distributed by a spinning reflector, such as a mirror, into a stationary array of filters and/or gas cells in sequence to an ellipsoidal mirror or an array of ellipsoidal mirrors that focus the light into a single detector. The visible and ultraviolet light is directed to one or more spectrometers that can analyze the desired wavelength ranges directly.

Figure 1:
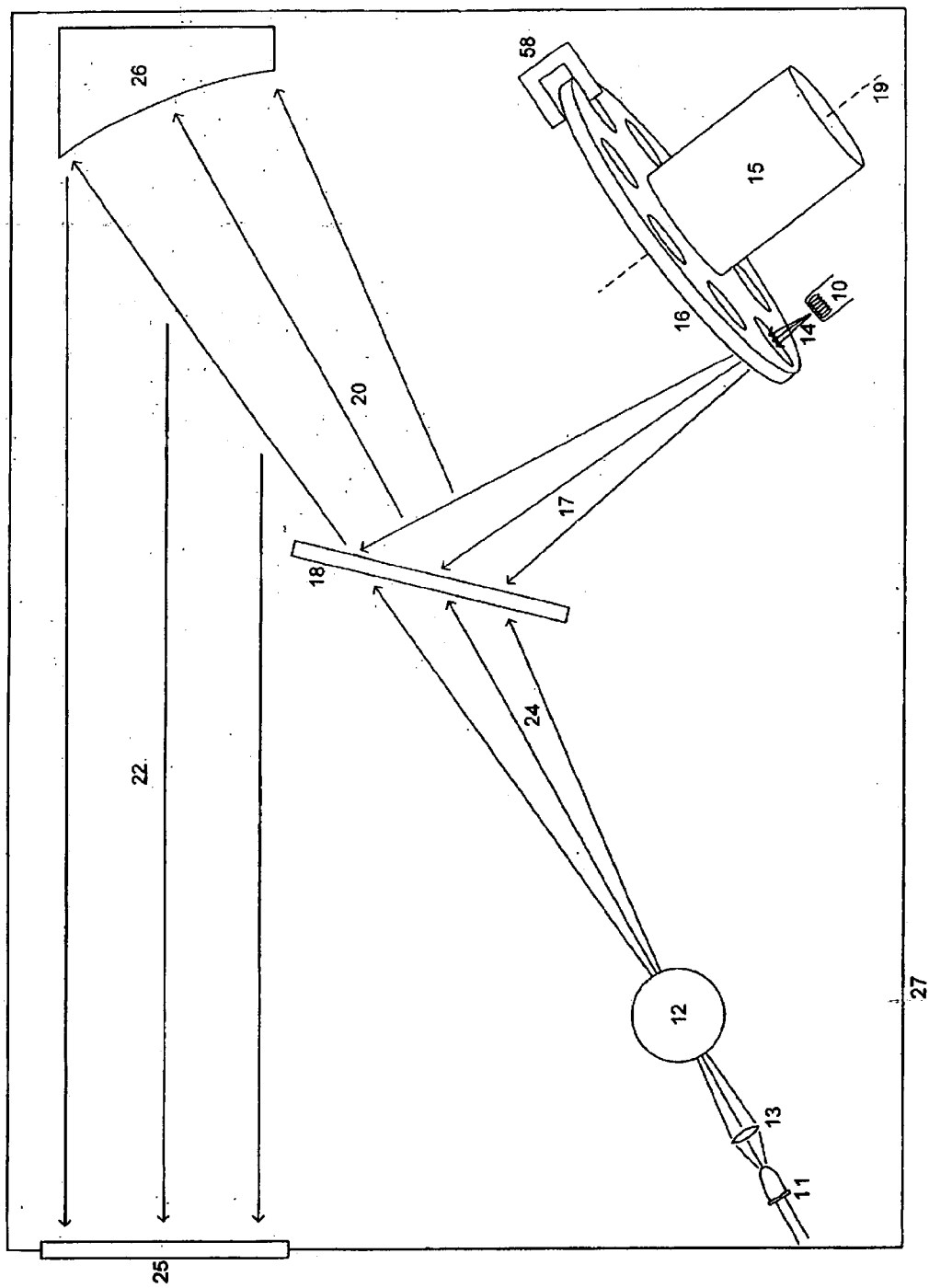
FIG. 1 illustrates a preferred embodiment of a source unit of the present invention including housing with window, light sources, filter wheel, beam splitter/combiner, and reflector.

A portion of a preferred embodiment of the present inventive apparatus is illustrated in FIG. 1. FIG. 1 illustrates a possible light source component of the present invention. The light source component shown includes an infrared light source 10, a source of visible light 11, and an ultraviolet light source 12. The infrared light 14 emitted by the infrared source 10 passes through a filter wheel 16, more completely described in FIG. 4. Then it is reflected by a beam splitter/combiner 18, and follows an optical path 20 until it reaches a reflector 26 such as an off-axis paraboloidal mirror or spherical mirror. An off-axis paraboloidal mirror is preferred over a spherical mirror due to the aberrations in light that occur with spherical mirrors, however production economics may dictate the use of spherical mirrors. The reflector 26 reflects the infrared light along a path 22, through a protective window 25 in the housing 27, leading to a reflection unit illustrated in FIG. 2.

The reflector 26 and other optical components described in this embodiment are protected by a window 25 that allows the transmission of all of the wavelengths of interest. This window 25 is attached to the housing 27 of the entire source unit. Preferably, the light sources and detectors are included within a single housing. However, the light sources and the light detectors may optionally be provided in more than one housing. Also preferably, the housings are sealed to prevent contaminants such as soot, road dust, and other road debris from damaging or coating the internal components and thus degrading the light signal received and/or transmitted by them. Also preferably, the sealed housings contain windows to allow light of the wavelengths of interest to leave and enter the housings as required for the light to travel along the desired optical path. These windows are preferably made of a material such as calcium fluoride ($CaF_2$), sapphire, or other material that will pass light of all wavelengths of interest with little or no attenuation. Optionally, the windows may be coated by a particular type of coating such as an anti-reflection coating or other suitable coating to enhance the transmission of light of the wavelengths of interest.

The infrared light source 10 may be any source that emits a sufficient intensity of light of the wavelengths of interest. The reflectors and optical path length determine the size of the spot from the infrared source that contributes to the light beam. Preferably the source is chosen, such that the light emitting area of the filament is as close to that spot size as possible for minimum power consumption.

Preferably, the filter wheel 16 is a spinning wheel that is powered by a motor 15 that spins the wheel 16 about an axis 19. Also preferably, a synchronization device 58 is provided to track the position and rotational speed of the filter wheel 16. Features of the filter wheel 16 are more completely illustrated in FIG. 4.

In addition, visible light from source 11 is focused by an optical element 13 to bring diverging light rays back into a focus through the center of ultraviolet source 12 where it is combined with the ultraviolet light from source 12 into a combined beam 24. The combined visible and ultraviolet light 24 passes through the beam splitter/combiner 18 such that it also follows optical path 20 to the reflector 26, where the light is reflected to also follow path 22 out window 25 toward the reflection unit illustrated in FIG. 2. The visible light source 11 may be a light emitting diode (LED), which emits light in a narrow range of wavelengths, or another visible source such as a halogen lamp that emits a broader range of wavelengths. The advantage of passing the visible light through the ultraviolet light source 12 is eliminating the need for another beam splitter/combiner, saving optical power that would otherwise be lost by the inefficiency of the beam splitter/combiner, in addition to saving space within the enclosure 27. However, if it is desirable to have an ultraviolet source 12 of a design that does not allow for pass-though of the visible light, then alternatively, the visible source 11, and ultraviolet source 12 may be reconfigured to take, for example, positions 146 and 144 as illustrated in an arrangement of sources in FIG. 13 that will be discussed further below.

The visible light source 11 is not required for gaseous measurements, however visible light is used to measure particulate matter and potentially opacity and lubricating oil elements. Particulate Matter having a diameter of 2.5 microns and smaller ($PM_{2.5}$) can be measured by an absorption technique at a wavelength of 500 nanometers, using a spectrometer such as in FIG. 3, element 42. Ideally, a $PM_{2.5}$ measurement would best be taken at 530 nanometers, however when measuring vehicle exhaust, there are interferences caused by gaseous species such as nitrogen dioxide ($NO_2$) that also absorb at 530 nanometers that would preclude obtaining a precise measurement of vehicular exhaust. This is especially true when measuring diesel exhaust as diesels emit a significant amount of $NO_2$ and particulate matter. $PM_{2.5}$ measurements at 500 nanometers include only elemental carbon and will therefore miss roughly 30% of the total concentration of diesel $PM_{2.5}$, but will not have any significant interferences with the precise measurement of $PM_{2.5}$ at this wavelength. Despite the penalty of missing 30% of the total diesel $PM_{2.5}$, this measurement can be scaled to provide a more accurate measurement when compared to other methods of detection.

Furthermore, the 500 nanometer wavelength was selected because of the desire to collect information about particulate mass for measurement of particulate emissions, in order to be consistent with the Federal reference method as summarized in BACKGROUND above. Focusing on the total mass measurement is done at the expense of measuring the total count of particles in exhaust, however the particles that are missed being measured by this embodiment are the smallest particles, and therefore do not contribute much to the total mass of the particulate sample.

This same $PM_{2.5}$ information can be used to determine whether a gasoline-powered vehicle is in a cold start mode. Cold start is when the engine of the vehicle being tested is not up to its normal operating temperature. A gasoline-powered vehicle in cold start mode will emit a much greater amount of particulates, on par with the amount of particulate emissions from diesel-powered vehicles, than a vehicle up to normal operating temperature. Cold start information is very useful for open-path emissions testing equipment, as it is important when enforcing air pollution laws not to falsely incriminate a tested vehicle for excess emissions when the vehicle is merely not operating in a normal mode. It is not possible to directly interrogate the driver of a tested vehicle using a non-intrusive method of sampling vehicle exhaust such as with an open-path method of a preferred embodiment. There is no means for stopping the vehicle to interrogate the engine's operating temperature or mode. The operating mode has to be deduced from several pieces of information, and cold start information is one element of this.

A second visible source in the approximate position of visible light source 11 can be added to the system to provide the ability to measure opacity, if no singularly suitable light source 11 can be obtained. The Society of Automotive Engineers J1667 opacity test, also known as the "Snap Acceleration Test", measures opacity concentrations in the range of 562 through 568 nanometers. This embodiment can include measurement of exhaust opacity per the apparatus requirements of the J1667 specification, with the variation being that the measurements occur in an open path configuration. Using a visible light source 11 in combination with a spectrometer means of detection 42 provides for detection of opacity over the entire range of wavelengths as specified in J1667, as opposed to current art that has a much narrower field of view spectrally.

As an alternative to having two visible light sources, the visible light source 11 can be selected with a sufficiently broad output of spectra such that $PM_{2.5}$, opacity, and even blue smoke can be measured. Blue smoke may be an indication that the vehicle is excessively burning lubricating oil, and therefore is in need of internal engine repairs to reduce emissions. This blue smoke plume comes as a result of lubricating oil combustion, and contains elements that are in the lubricating oil. Principal elements of lubricating oil that show up in the exhaust plume of a vehicle include sulfur, zinc, magnesium, copper, calcium, and phosphorus. The very high temperature combustion that occurs inside of a vehicle's engine temporarily causes these elements to appear in gas phase, when they can be viewed through an optical absorption technique. The wavelength of absorption for each of these elements is listed in Table 1.

Because of absorption interferences with gaseous emissions emanating from the same vehicle, some elements of the lubricating oil are better for observing than others. For instance, zinc absorbs ultraviolet light at 213.9 nanometers, which is unfortunately in the same general absorption vicinity as 1,3 butadiene and nitrogen monoxide. Both of these gases are present in tailpipe exhaust. Phosphorus however has an absorption wavelength in the visible spectra away from significant gaseous emissions interferences and is therefore a preferred method of determining a vehicle that is excessively burning its engine lubricating oil.

It is not essential to get a precise measurement of the amount of a lubricating oil element in the exhaust. The mere presence of the element, in significant concentrations that it is detected by the embodiment, is sufficient to provide probable cause that the tested vehicle is excessively burning lubricating oil. For this reason, there is no need to include the lubricating oil elements into a combustion equation that accounts for exhaust dilution.

Given that these elements have very narrow wavelengths of absorption on the order of 0.2 nanometers, it is preferred to use a laser source 11 directed to a discrete detector in place of a spectrometer 42 within this embodiment, as opposed to using a broadband source 11 and a visible spectrometer 42. However, a spectrometer 42 with sufficient resolution of the grating and enhancements to other supporting parameters such as the slit opening to the spectrometer 42, can provide a method for determining the above named elements that are present in combusted lubricating oil. For a visible spectrometer embodiment, an economy can be achieved by using the same spectrometer 42 for lubricating oil elements detection as is used for the J1667 equivalent test detection, though the J1667 test wavelengths do not require the small increment gradient as desired with the lubricating oil element detection. A broadband visible light source 11 can be used, when in combination with a spectrometer 42 for detection, to emanate light at wavelengths for lubricating oil elements that absorb in the visible spectra, along with emanating the J1667 wavelengths as disclosed above.

The ultraviolet light source 12 is preferably an ultraviolet lamp such as deuterium lamp, a xenon lamp, or another lamp that has ultraviolet light emission characteristics broad enough to include wavelengths of interest, ideally to emit light for at least all of the ultraviolet wavelengths of interest as listed in Table 1.

As FIG. 1 illustrates, where multiple light sources such as components 10, 11, and 12 are provided, the emitted beams preferably follow substantially the same optical path 20 toward the reflector 26. The reflector 26 is positioned such that light sources 10, 11, and 12 are near the focal point of the reflector 26 and the reflected light 22 is parallel to its axis of rotation. The angle between the incoming 20 and reflected light 22 and the focal length are determined by the design of the reflector 26 and may be chosen based on considerations of component layout and F-number. (F-number of an off-axis paraboloidal mirror is defined as the diameter of the mirror divided by its effective focal length.) Thus, light 20 transmitted to the reflector 26 is reflected in a direction 22 that is away from the original light sources 10, 11, and 12. In addition, if beam splitter/combiner 18 is a neutral density filter, it is preferably chosen so that the proportion of visible and ultraviolet light passed and the proportion of infrared light reflected are balanced according to the requirements of the detection unit. Optionally, a beam splitter/combiner 18 that is sensitive to different wavelengths such as a dichroic beam splitter may be used instead of a neutral density filter for beam splitter/combiner 18. In order to use some types of beam splitter/combiners, the positions of the infrared 10 and visible/ultraviolet sources 11, 12 may be reversed.

Figure 2:
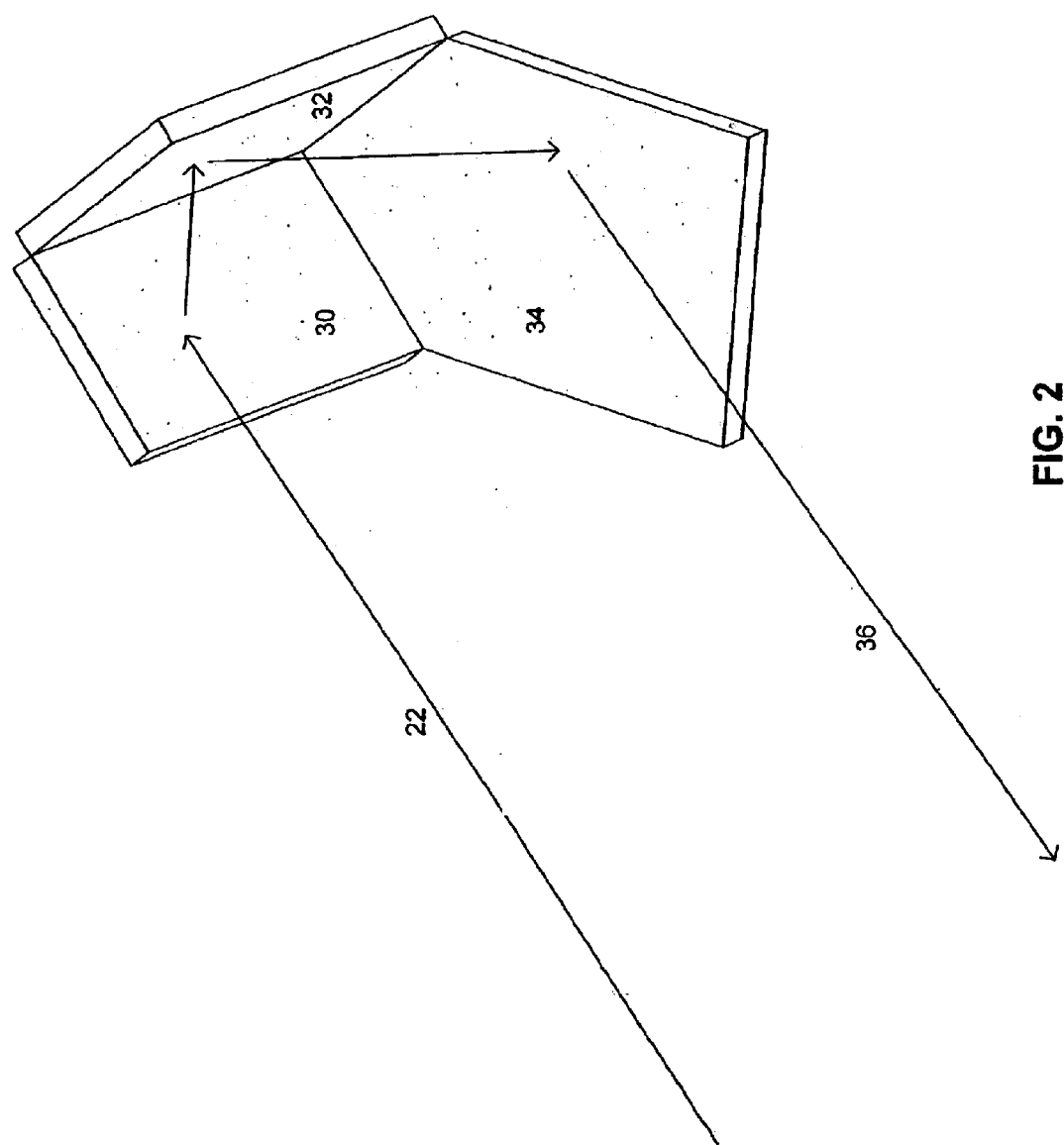
FIG. 2 illustrates a preferred embodiment of a reflection unit of the present invention.
Figure 9:
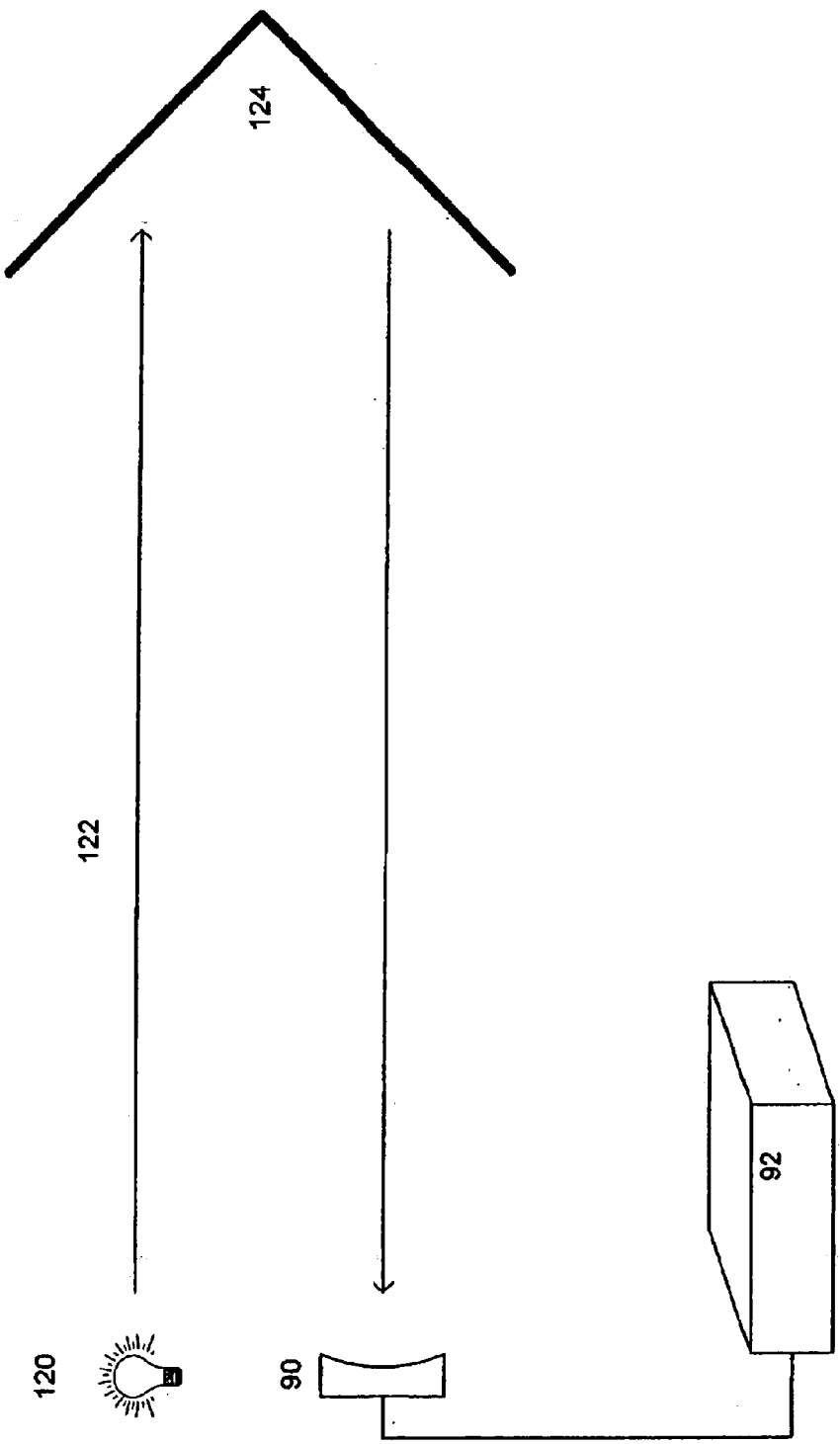
FIG. 9 is a conceptual diagram of some basic components of the present invention, including light source, reflection unit, detection unit, and processor.

FIG. 2 illustrates an exemplary reflection unit, which in an embodiment used to detect vehicle emissions is preferably placed across the road from the light source and detector components, creating an open-path emissions testing system. The reflection unit includes a retro-reflective system, preferably a vertical system, and preferably comprising three mirrors positioned to form 90° angles with respect to each other. A vertical orientation of the mirror assembly is preferred in order to adequately capture the emissions of vehicles of all profiles and heights. Referring to FIG. 2, incoming light 22 is reflected by a first mirror 30 and a second mirror 32. The first and second mirrors are adjacent or substantially adjacent to each other to form a 90° angle. The light reflected by the first and second mirrors is transmitted to a third mirror 34. As FIG. 2 illustrates, the flat reflective portion of third mirror 34 forms a 90° angle with the flat reflective portions of both first mirror 30 and second mirror 32. It is not important to have mirrors 30,32 on top of mirror 34, as this orientation could be reversed without any change to the quality of reflection of light. Light 36 that is reflected by third mirror 34 is then transmitted to the detection unit and travels in a direction that is parallel to the incoming light 22 in a configuration as illustrated in FIG. 9 to be discussed later in this text. The incoming light 22 and/or the reflected light 36 pass through an air component that is to be measured, such as vehicle emissions.

Figure 3:
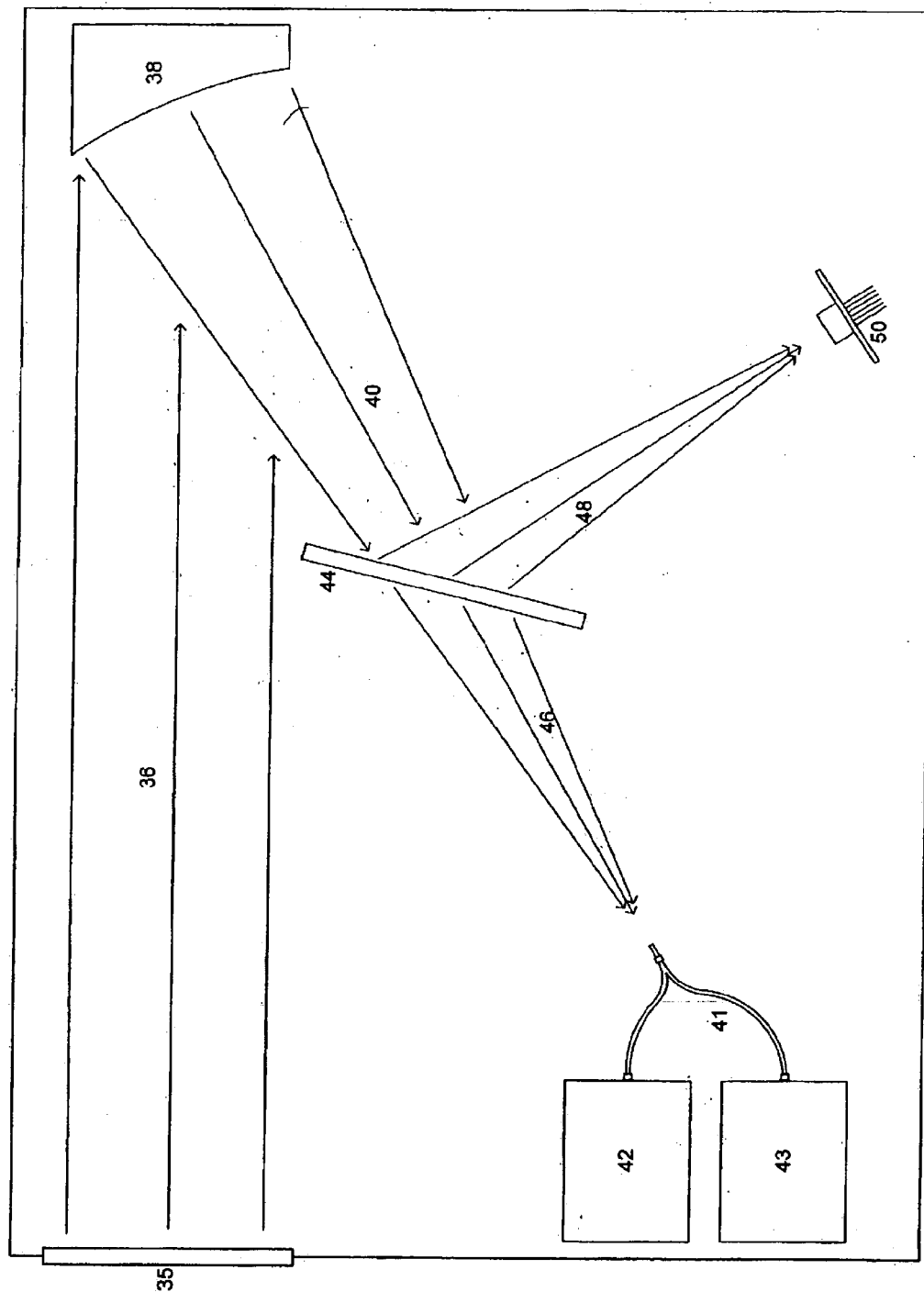
FIG. 3 illustrates a preferred embodiment of a detection unit of the present invention including housing with window, reflector, beam splitter/combiner, detector and spectrometers.

FIG. 3 illustrates an exemplary detection unit that receives the light that is generated by the source component of FIG. 1, and reflected by the reflection unit of FIG. 2.

Referring to FIG. 3, incoming light 36 passes through a protective window 35 that has similar characteristics to the window of the source unit illustrated in FIG. 1, is reflected by a reflector 38 such as an off-axis paraboloidal mirror or spherical mirror that reflects light along an optical path 40 at an angle relative to the incoming light 36. The light transmitted along the optical path 40 is reflected by a beam splitter/combiner 44 that directs infrared light 48 toward infrared detector 50. Preferably, the infrared detector 50 is positioned within the focal volume so that the light will over-bathe the detector's active area so that system vibrations will not adversely affecting measurements by causing a portion of the detector's active surface to temporarily not have light exposure. Focal volume is defined as the three-dimensional volume of light, in which the light is focused to its maximum intensity, in this instance infrared light 48, that travels to the detector 50. Maximum intensity of light occurs when all lights rays are concentrated into the smallest cross-sectional area of the focal volume. This cross-sectional area is not necessarily located at the focal point of the reflector 38, but is located farther away from the reflector 38 than the focal point.

Small, economical, durable, and versatile spectrometers 42, 43 are commercially available for most ranges of wavelengths of interest in the visible and ultraviolet regions. In the infrared region, however, spectrometers are less practical than individual detectors optimized for particular ranges of wavelengths. These infrared detectors are expensive and require cooling and complicated electronics for support. It is therefore a great advantage to use only a single infrared detector 50 in the detection unit. If separate detectors are used to detect the intensity of each wavelength or band of wavelengths of interest, the calibration problem caused by the different sensitivities of the different detectors must be addressed. This problem is further compounded because sensitivities change with time and temperature and can be different for each detector. Therefore a system using only a single infrared detector 50 is much simpler and is preferred.

The infrared detector 50 is preferably composed of mercury-cadmium-telluride (MCT), preferably utilizing at least three-stage thermal electric cooling. However, a lead-selenide or other composition detector can be used, and with greater or lesser staged cooling. A liquid cooled detector could also be utilized in this embodiment provided there is supporting equipment to accommodate the liquid cooling. Another possibility for cooling the detector is by Stirling Engine cooling, however this adds cost and complexity. The MCT composition detectors offer a more compatible electronic biasing consistent with reduced noise than other composition detectors. Other factors considered for single detector selection is the detectivity, commonly expressed in terms of "D*", responsivity to light, the timing of the pulses of light to which the detector is exposed, and the saturation level.

This embodiment also prefers the economy of a photo-conductive type of single detector as opposed to the more expensive photovoltaic detector. While photovoltaic detectors comparably offer less noise in lower pulse frequencies, this is not an issue for this embodiment as it is desirable to stimulate the detector with as high a frequency that the spinning filter wheel illustrated in FIG. 1 item 16, or spinning reflector illustrated in FIG. 5 item 62 will allow.

Lastly, a detector needs to be selected to respond to light consistent with the range of desired wavelengths. A range of mid-infrared wavelengths for this embodiment can be viewed in Table 1 which suggests a detector sensitivity range of wavelengths between roughly 3–5 microns. However, if alternative wavelengths are used for such embodiment to measure the gases of interest, the desired range of wavelengths to which the detector is sensitive may have to be adjusted.

If the range of infrared wavelengths of interest is too broad for a standard detector, a dual substrate detector may be used. A commercially available dual substrate detector contains two different semiconductor compounds, each sensitive to slightly different ranges of wavelengths. They are mounted in a single detector package, one in front of the other so that their active areas nearly coincide. Thus the combination performs as if it were a single detector with sensitivity to a broader range of wavelengths than would otherwise be possible.

The beam splitter/combiner 44 may comprise any reflective or transmissive device, such as a neutral density filter, which transmit a specified fraction of the incident light and reflect almost all of the rest, treating a broad range of wavelengths equally, or dichroic beam splitter/combiner that can be designed to reflect almost all of the incident light of a specific range of wavelengths, and transmit almost all of the rest. The beam splitter/combiner 44 passes all or portions of visible and/or ultraviolet light 46 so that the visible and ultraviolet spectra may be measured by one or more spectrometers 42, 43. The light which passes through beam splitter/combiner 44 is split off and carried to the respective spectrometers in one of two ways. The first, illustrated in FIG. 3, is to focus light onto the end of a Y-shaped optical fiber cable 41 that first receives the light in a single open end of the fiber optic cable, then divides the light within the cable sending a portion of the light to each spectrometer.

Figure 7:
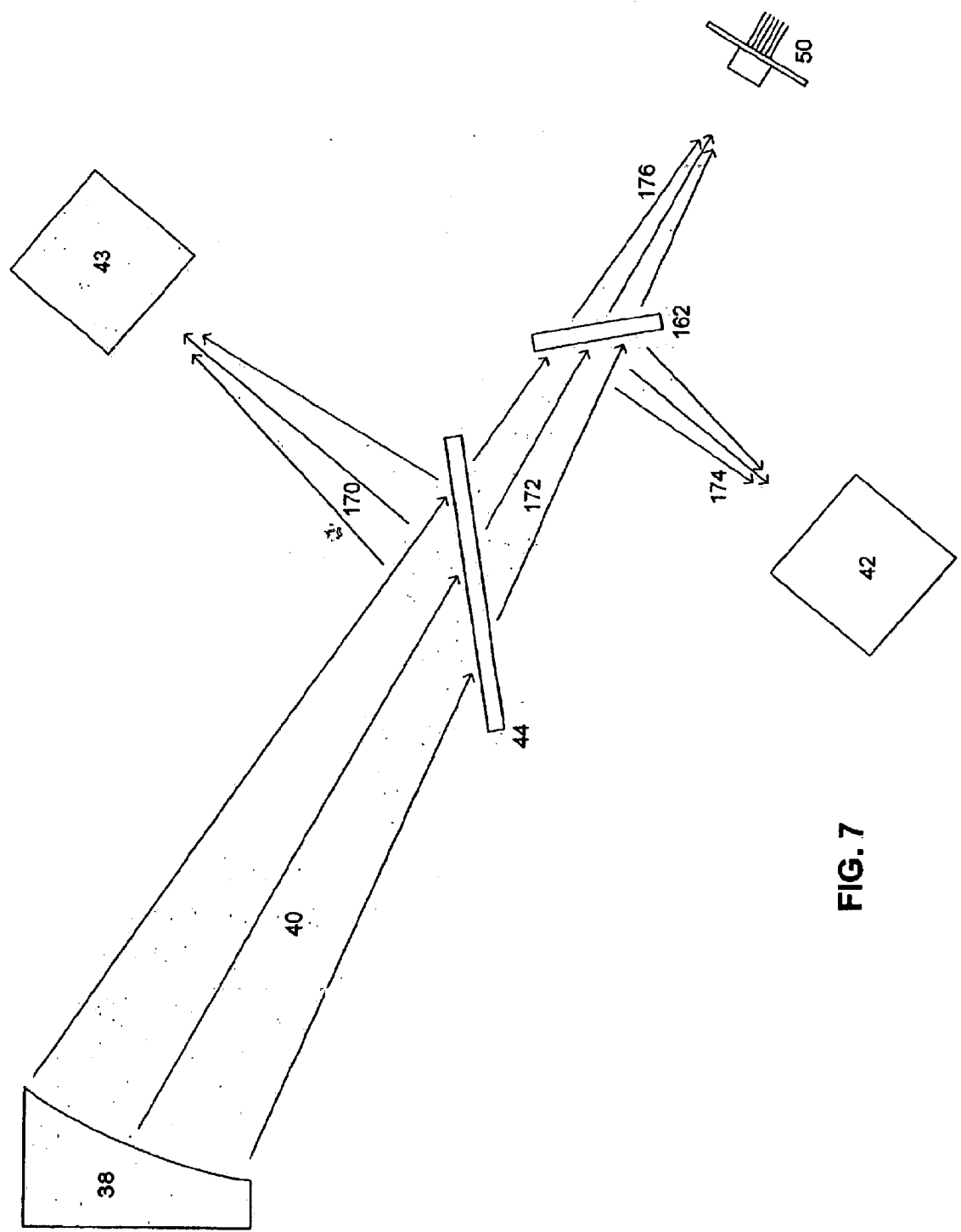
FIG. 7 illustrates a detection unit using multiple spectrometers and a single detector.

An alternative method of splitting the light to two or more spectrometers, illustrated in FIG. 7, is to use separate beam splitter/combiners 44 and 162 to split light beam 40 twice. Beam splitter/combiner 44 first splits beam 40 into beams 170 and 172. Beam 170 is focused directly into the opening of spectrometer 43 while beam 172 continues on to beam splitter/combiner 162. Beam splitter/combiner 162 then splits beam 172 into beams 174 and 176. Beam 174 is focused on spectrometer 42 while beam 176 continues on to be focused on the infrared detector 50. In either embodiment, whether cable splitting of light as illustrated in FIG. 3 or multi-beam splitting method of FIG. 11, the light slightly over-bathes the opening to the optical fiber cable (FIG. 3 item 41) or the light orifice of the spectrometer 42,43 for resistance to vibration and coincident reduction of light intensity with the vibration for similar reasons as expressed above for the infrared detector 50.

TABLE 1

List of Some Example Tailpipe Emissions Channels and their Wavelengths

| Component | Wavelength |
|---|---|
| Carbon Monoxide (CO) | 4.65 $\mu$ |
| Carbon Dioxide (CO$_2$) | 4.30 $\mu$ |
| HC$_1$ (Alkane series hydrocarbons) | 3.45 $\mu$ |
| Methane (CH$_4$) | 3.31 $\mu$ |
| HC$_2$ (Alkene series hydrocarbons) | 3.17 $\mu$ |
| HC$_3$ (Alkyne series hydrocarbons) | 3.01 $\mu$ |
| H$_2$0$_{(v)}$ | 2.90 $\mu$; 2.64 $\mu$ |
| Phosphorus (P) | 0.6400 $\mu$ |
| Elemental Carbon of PM$_{2.5}$ | 0.500 $\mu$ |
| Calcium (Ca) | 0.4227 $\mu$ |
| Copper (Cu) | 0.3247 $\mu$ |
| Magnesium (Mg) | 0.2852 $\mu$ |
| Nitrogen Monoxide (NO) | 0.226 $\mu$ |

TABLE 1-continued

List of Some Example Tailpipe Emissions Channels and their Wavelengths

| Component | Wavelength |
| --- | --- |
| Zinc (Zn) | 0.2139 µ |
| 1,3 Butadiene ($C_4H_6$) | 0.210 µ |
| Ammonia ($NH_3$) | 0.208 µ |
| Reference | 3.90 µ |

Figure 4:
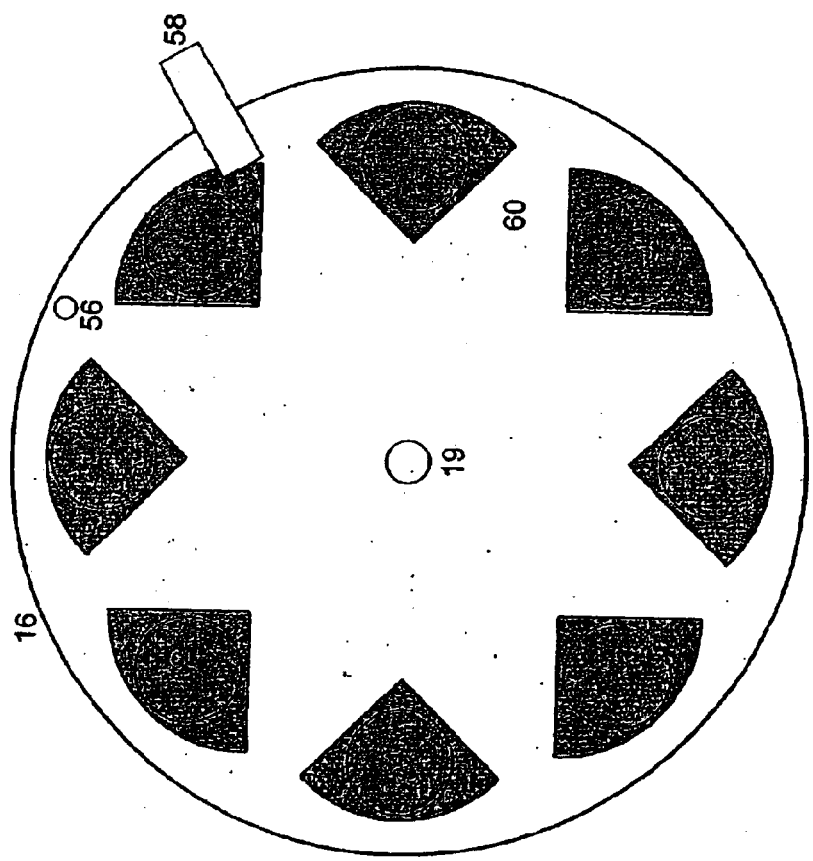
FIG. 4 illustrates an exemplary filter wheel that may be used in accordance with one embodiment of the present invention.
Figure 6:
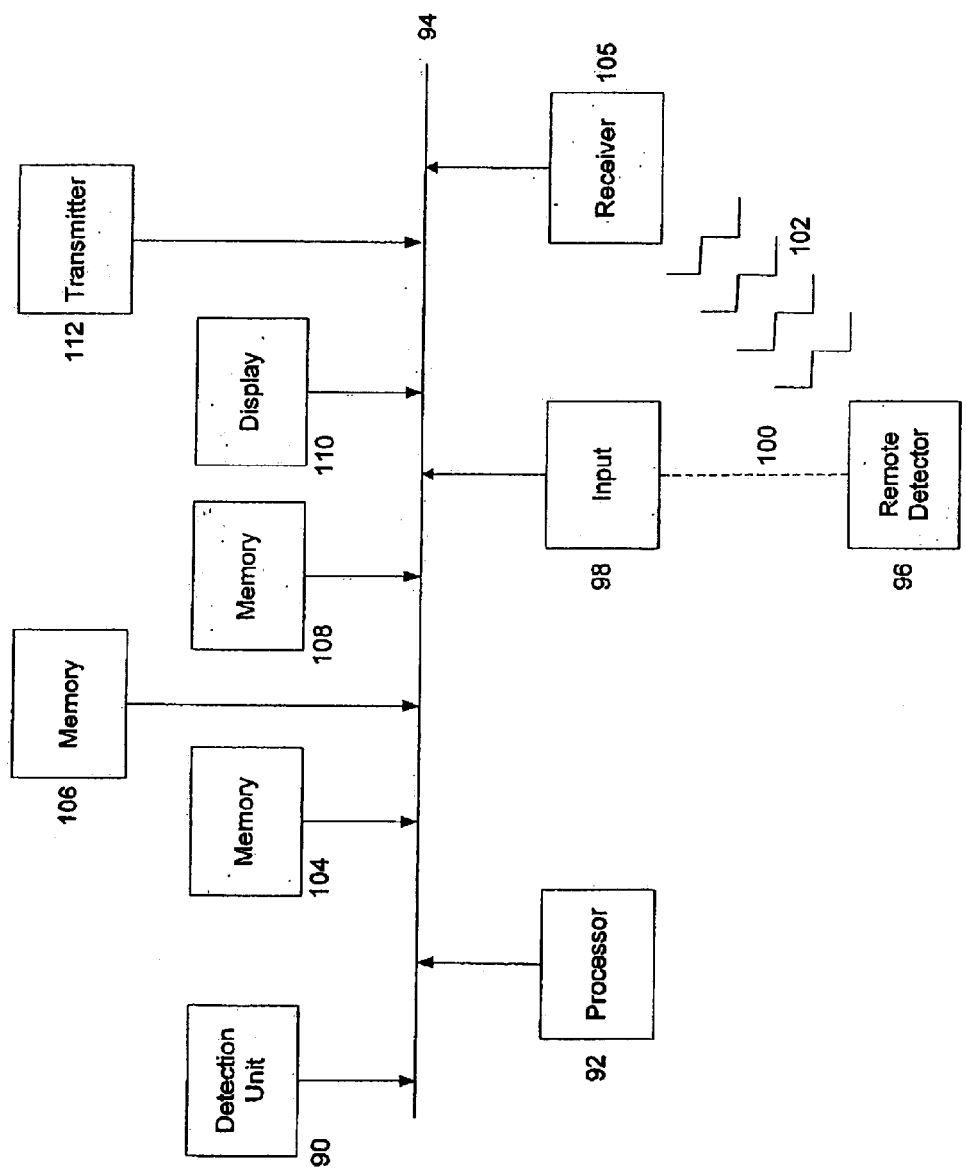
FIG. 6 illustrates several elements of an exemplary computer of a type suitable for carrying out certain functions of the present invention.

In a preferred embodiment, the transmission and detection of light at the wavelengths of mid-infrared listed in Table 1 is accomplished by using a spinning filter wheel as the filter component (referred to in FIG. 1 as item 16). FIG. 4 illustrates an exemplary spinning filter wheel. Referring to FIG. 4, the spinning filter wheel contains light filters such as 52 that correspond to wavelengths associated with individual emission components, such as those illustrated in Table 1. One of the filters 54 must correspond with a wavelength at which no gaseous absorption takes place. Such a filter is known as a "reference" filter 54. The light intensity measured from the reference filter 54 is used to normalize the light intensity measured from each of the gaseous filters 52, so that concentrations of those gases may be calculated by a processor (FIG. 6 item 92). FIG. 4 illustrates a wheel having eight filters 52, 54 each utilizing one of the mid-infrared wavelengths of Table 1, however fewer and/or additional filters, corresponding to fewer and/or additional vehicular exhaust constituents, may be used in alternate embodiments. Each filter 52 is designed to allow light of a specific range of wavelengths to pass through it.

Another innovation regarding the filters 52,54 is that they are quadrants of an industry standard 25 millimeter optical filter. The round, 25 millimeter diameter filters are cut into four pie shapes allowing for filters to cost one-fourth of what they would otherwise cost if an entire industry standard sized filter were to be inserted in each of the open positions on the filter wheel 16. In addition to cost, there is a savings in the amount of rotating mass by quartering the industry standard sized filters that the wheel 16 would have if the filters were installed whole. Lastly, special slots exist in the wheel 16 to allow for a two-piece optical filter 52,54, should this be necessary. There are occasions when a filter manufacturer will supply two filters in order to provide the desired band pass of wavelengths to measure a gas of interest. The wheel 16 has the capability to accept these two-piece filters.

In addition, the filter wheel preferably will have one or more synchronization marks 56 that may be detected by a synchronization unit 58 to define either the exact filter or the start of a sequence of filters that will be in the optical path. The wheel 16 must have an opaque area 60 between each filter. The opaque areas 60 prohibit source light (FIG. 1 item 10) from getting to a detector when the opaque areas 60 pass in front of the infrared source (FIG. 1 item 10) transforming the incident light beam into a sequence of pulses (FIG. 1 item 17). In operation, the wheel spins about an axis 19 at high speeds, preferably at least 12,000 rotations per minute, to form a sequence of infrared light pulses (FIG. 1 item 17). Faster rotational speeds are even more preferable since they increase the sampling rate of the emission medium. The increased pulse rate to the detector 50 provides a higher signal to noise response. The synchronization unit (FIG. 1 item 65) allows the processor (FIG. 6 item 92) to associate a wavelength of interest, and corresponding gas of interest, with each pulse of light seen by the detector (FIG. 6 item 90). This combination overcomes disadvantages of prior art, which require discrete detectors for each wavelength.

Figure 5:
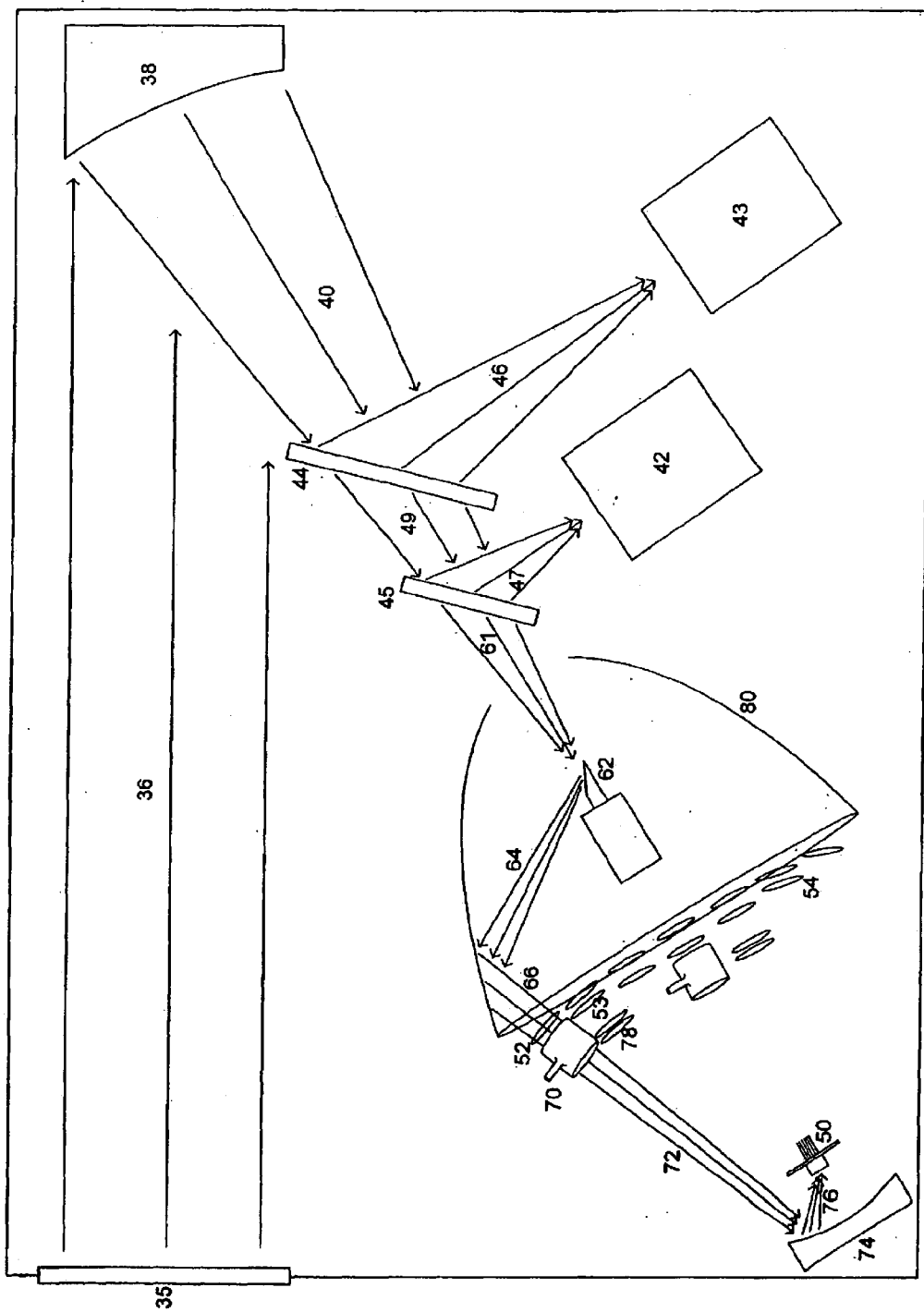
FIG. 5 illustrates an alternate embodiment of a detection unit of the present invention including housing with window, reflector, beam splitter/combiners, spectrometers, spinning reflector, monolithic ellipsoidal mirror, filter array with gas cells, focusing reflector, and a single infrared detector.

In accordance with an alternate embodiment of the present invention the light source unit illustrated in FIG. 1 may omit the spinning filter wheel assembly 15,16,19,58. In this embodiment, an alternate detector unit is provided as illustrated in FIG. 5. Incoming light 36 transmitted from the source unit of FIG. 1 and reflected by the reflection unit of FIG. 2 passes through window 35 that has similar characteristics to window of source unit illustrated in FIG. 1, and is reflected by a reflector 38, which directs the light beam 40 onto beam splitter/combiners 44,45 which direct portions 46,47 of the light to the spectrometers 43,42. The rest of the light 61 is focused on spinning reflector 62. Reflector 62 is a single faceted flat mirror with a reflective surface that is optimized for the infrared light wavelengths of interest, such as an enhanced gold reflective surface or other suitable reflective surface. Alternatively, a multifaceted spinning mirror may be used, however the geometry of the rest of the layout would have to be modified from what is illustrated in FIG. 5. The spinning reflector 62 splays the light in sequence around a stationary array of filters 52,53,54 and gas cells 70 by directing the beam 64 into the side of monolithic ellipsoidal mirror 80 which reflects the light 66 into the array, consistent with the splaying of the light. After passing through each stationary band pass filter 52,53,54 and gas cell 70, the light beam 72 is redirected to and focused on a single infrared detector 50 by a reflector 74 such as a spherical mirror. The reflective surfaces of reflectors 80 and 74 are optimized for the wavelengths of interest in the same way as the surface of spinning reflector 62. The single infrared detector sees a sequence of pulses of light 76 that are essentially the same as those illustrated as FIG. 3 item 48. Each filter 52,53,54 of this array substantially limits the passage of light to a predetermined spectral wavelength or range of wavelengths. Some filter center wave specifications are listed in Table 1. Each gas cell 70 of this array substantially limits the passage of light of a particular spectral pattern of wavelengths absorbed by the known concentration of the gas of interest that the cell 70 contains.

Another advantage of this embodiment is that there is much less rotating mass in the spinning reflector 62 than in the spinning filter wheel illustrated in FIG. 4. Therefore the spinning reflector 62 can be spun at a much faster rate than the spinning filter wheel illustrated in FIG. 4. Faster spin rate corresponds to a higher sampling rate that can contribute to lower electronic and optical noise levels, and provide better time resolution of a plume of vehicle exhaust constituents.

Figure 8:
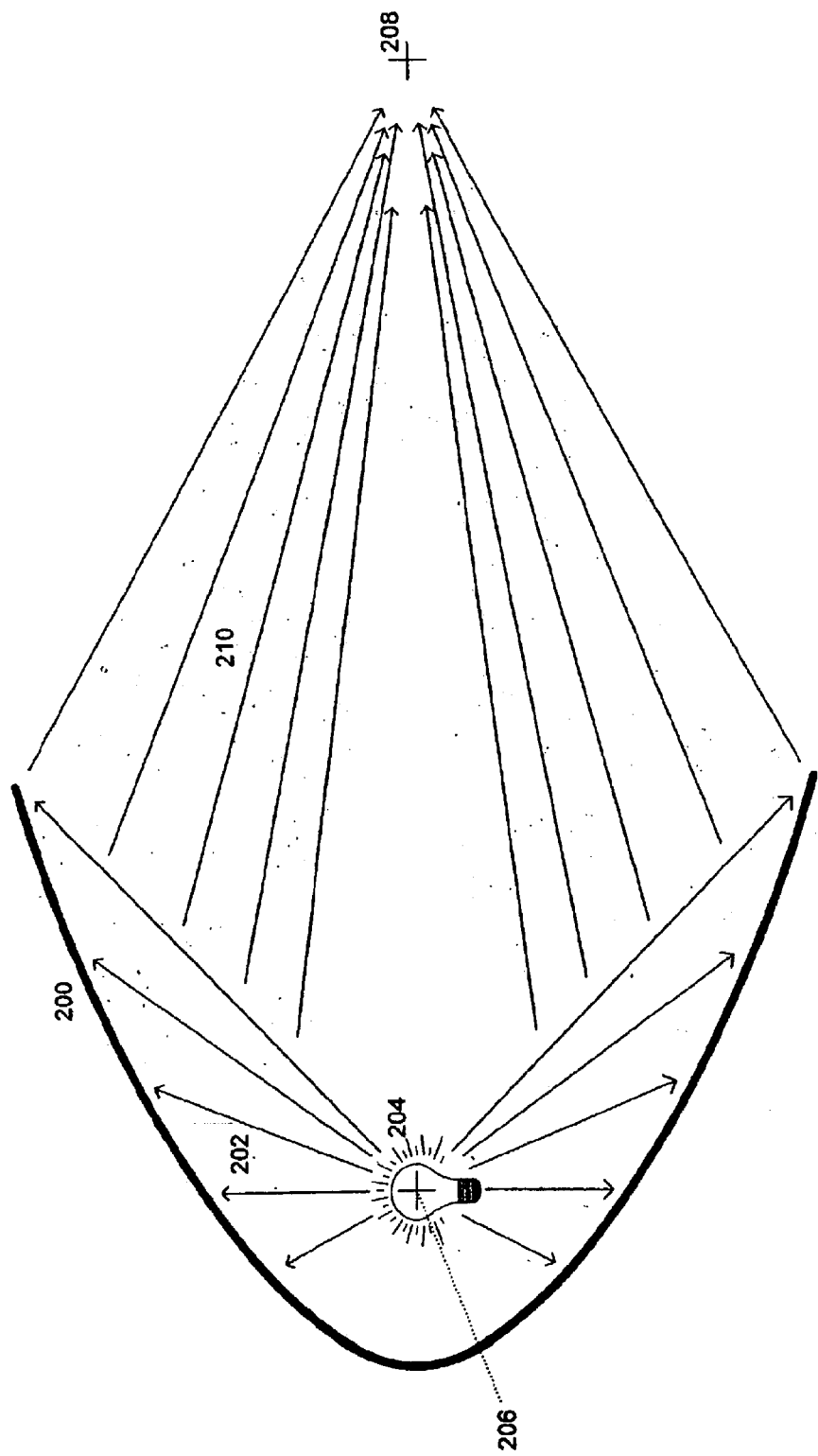
FIG. 8 illustrates the properties of an ellipsoidal reflector.

It is instructive to refer to the illustration of FIG. 8 to further the understanding on why an ellipsoidal mirror (FIG. 5 item 80) is chosen to distribute light. An ellipsoidal mirror 200 has two focal points or foci 206,208. Such mirrors have the property that all light rays 202 diverging from a small spot near one focal point 206 are reflected in such a way that those rays 210 are again focused into a small spot near the other focal point 208 of the mirror 200. Given the unique layout of the alternative embodiment of FIG. 5, and commensurate need for a dual foci reflective device for light distribution through a full 360° of rotation of the spinning reflector (FIG. 5 item 62), an ellipsoidal mirror is the best choice for this alternative embodiment.

An alternative embodiment replaces the monolithic ellipsoidal mirror 80 with individual ellipsoidal mirrors and may place the filters 52,53,54 and gas cell 70 array before the individual ellipsoidal mirrors if layout and construction is simplified. This alternative can provide the advantage of the system suffering less light loss through use of individual mirrors as opposed to the monolithic ellipsoidal mirror 80. The disadvantage is that there may be more adjustments required in order to have the system of FIG. 5 properly aligned such that all light through the system is optimized.

FIG. 6 illustrates several elements of a computer processing device that may be used in accordance with a preferred embodiment of the present invention. Referring to FIG. 6, the detection unit 90 delivers emissions-related data to a processor 92. The detector may be any of the detectors or spectrometers as illustrated in FIGS. 3 and 5, or any device that receives or contains information collected by such detectors or spectrometers. Such detector systems for the purpose of discussion in FIG. 6 include a means for amplifying and converting the detector signals into digital signals that can pass to the processor 92 via a direct link such as a parallel data bus 94.

In this embodiment, the detection unit 90 is part of the unit that contains the processor 92, and the delivery is performed over a parallel bus 94 such as that which can be found in AT, ATX, EBX, and other motherboard styles upon which computers are based. However, the processor 92 and detection unit 90 may be separate, such as with the remote detector 96 illustrated in FIG. 6. Where a remote detector is used, the data may be delivered to the processor 92 by a communications link 100 that delivers the data to an input port 98 such as a communications port. A wireless communications link 102 and receiver 105 for such a wireless communication are also illustrated in FIG. 6. The communications link 102 may be a direct wire, an infrared data port (IrDA), a wireless communications link, global communications network such as the Internet, or any other communications medium.

The system illustrated in FIG. 6 also includes a memory 104 which may be a memory device such as a hard drive, random access memory, or read only memory. A portion of this memory 104 can contain the instructions for the processor 92 to carry out the tasks associated with the measurement of vehicular emissions. Preferably, concentrations of gases may be derived using the Beer-Lambert Law, however other tests and formulae may be used in alternate embodiments.

The Beer-Lambert Law, as disclosed in other art, relates absorbance of light to a concentration of gas where an amount of change in light intensity at a known wavelength is proportional to the concentration of a gas of interest at the wavelength of light where the gas is absorbed. The Beer-Lambert Law is expressed in terms of transmittance in Equation 1.

Equation 1: Beer-Lambert Law $$2 - \mathrm{Log}_{10}(\%T) = \varepsilon C l$$

Where:

% T is the amount of light transmitted through open air and the emissions sample expressed in percent units;

$\varepsilon$ is the absorption coefficient for the gas of interest at a corresponding wavelength of absorption;

C is the concentration of the gas of interest expressed in parts-per-million (ppm)

l is the path length expressed in meters.

Transmittance is further expressed as the amount of light that passes through the gas of interest in proportion to the amount of light that was originally emanated from the light source unit as illustrated in Equation 2. If a broadband optical filter is used in conjunction with a detector, there will be some residual light remaining that arrives at the detector even though the gas or emission of interest is at sufficient concentration to be at 100% absorbance. This is due to the fact that a broadband filter will pass light of wavelengths outside of the wavelengths of interest that are associated with a gas or emission of interest. For this embodiment, the transmittance equation is modified to subtract the amount of residual light at 100% absorbance of the gas or emission of interest. The correction for residual light most likely is not necessary for embodiments that utilize Tunable Diode Lasers or other similar methodology, as this methodology can measure in narrow enough wavelengths to not have residual light at 100% absorbance of the gas or emission of interest. Background transmittance of light can also be accounted for in Equation 2 in order to account for variations in background concentrations, and their associated absorbances. Furthermore, source variations can and should be accounted for, as a simple change in light intensity from a light source could be misinterpreted as a concentration of a gas or emission of interest.

Equation 2: Transmittance as Expressed in Percent $$\% \ T = \frac{I_p}{I_o} \times 100$$

Where:

$I_p$ is amount of light left after passing through the gas sample of interest $I_o$ is the amount of light that was originally sent through the entire sample path and not absorbed by the gas of interest The specific application of Beer-Lambert Law for this embodiment is found in Equation 3. Equation 3 is an algebraic substitution of transmittance "% T" (Equation 2), and subsequent manipulation of Beer-Lambert Law of Equation 1 to solve for a concentration of a gas in an open path, as this is the unknown for which this embodiment measures.

Equation 3: Application of Beer-Lambert in this Embodiment $$C = \frac{2 - \mathrm{Log}_{10}\left(\frac{I_p}{I_o} \times 100\right)}{\varepsilon \times l}$$

The concentrations calculated in Equation 3 are expressed in units of parts per million (ppm) for gaseous measurements, or micromoles/mole for particulate measurements. The correlation coefficient is empirically derived per acceptable methods of empirical establishment of a correlation coefficient for each gas of interest and $PM_{2.5}$ absorption. Equation 4 illustrates the conversion needed to go from a measurement in units of micromoles/mole to micrograms per cubic meter ($\mu g/M^3$) at Standard Temperature and Pressure (STP), the standard units for a typical $PM_{2.5}$ measurement. Temperature measurements of the measurement path are read or converted in the preferred embodiment to degrees Kelvin (° K) or other suitable temperature scale which has a lower limit at absolute zero. Pressure measurements of the measurement path are read directly or converted in the preferred embodiment to atmospheres (atm). The units conversion preferably takes place in the processor 92 immediately after the $PM_{2.5}$ measurement has been taken, however this is not essential to measurement accuracy.

Equation 4: Units Conversion for $PM_{2.5}$ Measurements $$Concentration\left[\frac{uMoles}{Mole}\right] = \frac{12.01 \text{ g} \times 1 \text{ Mole} \times 1000 \ 1 \times 10^6 ug}{1 \text{ Mole} \times 22.4 \ 1 \times 1 \text{ M}^3 \times 1 \text{ g}} \times$$

$$\frac{Temp_{amb}}{Temp_{@STP}} \times \frac{Press_{@STP}}{Press_{amb}}$$

$$= \frac{5.36 \times 10^8 ug}{M^3}$$

Other memory devices 106 and 108 such as additional hard disk storage, a CD-ROM, CD-RW, DVD, floppy drive, ZIP® drive, compact flash compatible device such as that which conforms to IBM Microdrive™ specification, or other memory device may also be included. An internal memory device 106 can be used to extend the number of emissions tests that can be conducted and retained by this preferred embodiment. A removable memory device 108 can be used to make the emissions data portable to allow for the emissions data to be further processed in a centralized location. The device also optionally and preferably includes a display 110 and/or a transmitter 112 for providing output to a user or another device.

Utilizing a computer processor 92, the intensity measured by the detector unit 90 at a wavelength of interest is compared by the processor 92 to the intensity of light detected by the detector unit 90 at a reference wavelength where no absorption of gases occurs. This method of detection is commonly known as Differential Optical Absorption Spectroscopy (DOAS). This DOAS methodology is a simple, inexpensive means of determining a concentration of a gas of interest emanating from a vehicle tailpipe in open air, and has examples in other art and fields of invention.

Alternatively, again using a computer processor 92, the intensity measured by a detector unit 90 at a desired wavelength for an interval of time, followed by measuring light at the detector unit 90 for an interval of time at the same desired wavelength with additionally a gas cell of known concentration of gas that absorbs light of the same wavelength can also be used as a methodology to determine a concentration of a gas of interest. This method of detection is commonly known as Gas Filter Correlation Radiometry (GFCr), and is documented in other art. GFCr has the potential to provide improved precision & accuracy of measurements due to the fact that the methodology allows for the constant referencing of a measurement to a known concentration of the gas of interest.

A preferred embodiment of FIG. 5 shows both DOAS and GFCr methods of determining a concentration of a gas of interest contained within the same embodiment. For example, an optical filter 53 can be optimized for sampling carbon dioxide ($CO_2$). Another filter 54 can be optimized to pass wavelengths of light where no absorption of $CO_2$ or other gases exist; such a filter is used for reference to assess the amount of light that passes through the sample path without $CO_2$ influence. As the amount of $CO_2$ concentration increases, the amount of light that the detector 50 observes through filter 53 will decrease, while the amount of light that the detector 50 observes through the reference filter 54 will remain unchanged. This is the fundamental of the DOAS methodology by comparing the amount of light ($I_p$ in Equations 2 and 3) off from the $CO_2$ filter 53 to the amount of light ($I_o$ in Equations 2 and 3) from the reference filter 54. Switching the light paths between the $CO_2$ path, created by filter 53 to detector 50, and reference path, created by reference filter 54 to detector 50, is accomplished by the spinning reflector 62 that splays the light for periods of time between the two mentioned paths and other paths that exist in this embodiment.

DOAS methodology is also provided in the embodiment illustrated in FIG. 1, however the light path switching is performed by the spinning filter wheel 16 such that, for a moment in time, the filter wheel rotation exposes an optical filter (FIG. 4 item 52) to light (FIG. 1 item 10) for a gas of interest, then for a roughly equal interval of time, the filter wheel exposes a reference filter (FIG. 4 item 54) to the same light (FIG. 1 item 10).

The GFCr methodology is provided in this embodiment as well. Expanding on the DOAS example above, a $CO_2$ filter 53 can be paired with another similar characteristic $CO_2$ filter 52 with the difference that the $CO_2$ filter 52 has a windowed small cell 70 that contains a sample of $CO_2$ gas. The amount of gas in the cell 70 is chosen based on the amount of optical depth that is desired with which the non-celled optical path is compared. The $CO_2$ filter 53 must have balancing windows 78 of the same optical characteristics as the gas cell 70 in order to make the amount of light between both light paths roughly equivalent. An alternative embodiment to the balancing windows 78 can use a second gas cell 70 in place of the balancing windows 78, but with all air evacuated to a vacuum, or air replaced with nitrogen or other inert gas at partial pressure to provide the optical balance. If a gas is used to fill the balancing cell, the gas cannot have absorption characteristics similar to the gas of interest being measured.

The balancing windows 78 are added to create an optical balance for the two $CO_2$ detection paths in the example given, such that the only difference in intensity of light to the detector 50 between the two paths is a change in concentration of the gas of interest. For a period of time, the light travels through the $CO_2$ filter 52 with $CO_2$ gas cell 70 and reaches the detector 50. In another time interval of approximately same length, the light will travel through the other $CO_2$ filter 53 with balancing windows 78 and on to the detector 50. Since the gas cell 70 contains a known concentration and corresponding optical depth of a sample of $CO_2$, the amount of light in the filter 52 to gas cell 70 to detector 50 path of light exists as a reference to which the amount of light from light path filter 53 to balancing windows 78 to detector 50 is compared. The amount of absorbance from each $CO_2$ light path is compared to determine a concentration of $CO_2$ in this example. As with the DOAS method of detection, light path switching is accomplished by the spinning reflector 62 that provides light to each mentioned path for a period of time in addition to making light paths for other gas sampling paths of this embodiment.

The unique advantage of GFCr is that any interferences to measuring a concentration of $CO_2$ in this example appear in both $CO_2$ light paths and therefore is commonly rejected among both light paths. Common mode rejection of interferences does not necessarily happen with the DOAS method of detection of gases, because of the use of a reference filter at a different wavelength, an interference could conceivably absorb light at the reference wavelength but not at the wavelength corresponding to the gas of interest. Also, the characteristics of the reference filter 54 are different from the other filters 52,53, and create a situation where different filters 52,53,54 pass different wavelengths of light, to which the detector 50 will have greater or lesser sensitivity to such wavelengths. With proper optimizations, these effects may be minimized, but not eliminated.

It should be noted that it is not necessary to have both DOAS and GFCr methodologies utilized in an embodiment in order to obtain reasonable measurements of concentrations of gases of interest. However it is desirable to have both when economically feasible in order to provide for improved precision and accuracy of measurements. Furthermore, although an example was given here for $CO_2$, it is possible to utilize GFCr for other gases including but not limited to carbon monoxide (CO), methane ($CH_4$), and any gas of interest that can be stored over long periods of time in a gas cell without the reference gas of interest degrading, attacking the walls of the cell and compromising the sample, or the reference gas combining with contaminants within the cell causing the reference concentration to no longer be known. GFCr methodology also is beneficial for speciation of hydrocarbons, as the gas cell 70 can be utilized as a sort of notch filter to indicate a particular gas of interest from a group of gases such as hydrocarbons.

Referring back to FIG. 6 the processor 92 of the embodiment, coupled with the appropriate instruction set contained within memory 104, can be capable of conducting either DOAS, GFCr, or simultaneously both methodologies of detection of concentrations of gases and then applying the concentrations to a combustion equation. Previous art in this field of invention has documented combustion equations that utilize ratioing concentrations of gases of interest relative to carbon dioxide ($CO_2$) to correct for any dilution effects in the exhaust stream of the vehicle being tested. The memory 104 can contain combustion equations unique to different fuels used to power vehicles that are tested by this preferred embodiment. Determination of the type of fuel used to power a tested vehicle can be done in the processor 92 at the time of measurement of the tailpipe emissions, or after emissions testing activities have concluded at the monitoring site in a centralized data processing facility. A method for determining the type of fuel of a vehicle is disclosed in U.S. patent application Ser. No. 09/928,720 entitled "METHOD AND SYSTEM FOR DETERMINING THE TYPE OF FUEL USED TO POWER A VEHICLE", filed Aug. 13, 2001, the disclosure of which is hereby incorporated by reference in its entirety.

FIG. 9 illustrates a preferred embodiment including a light source 120 capable of emitting at least one beam of light 122 having known emission intensities corresponding to one or more of infrared, visible, and ultraviolet spectra. The system also includes a reflection unit 124, a detection unit 90 capable of receiving the beam and measuring received intensities corresponding to the light spectra, and a processor 92 capable of comparing received intensities and identifying a concentration of a gas of interest. The light 122 is transmitted through a gas, such as air containing vehicle emissions, reflected, then detected for analysis and measurement of the amount of absorption that has occurred at known wavelengths. The amount of absorption may be used to determine concentrations of gases and particulate matter corresponding to the specific wavelengths.

Figure 10:
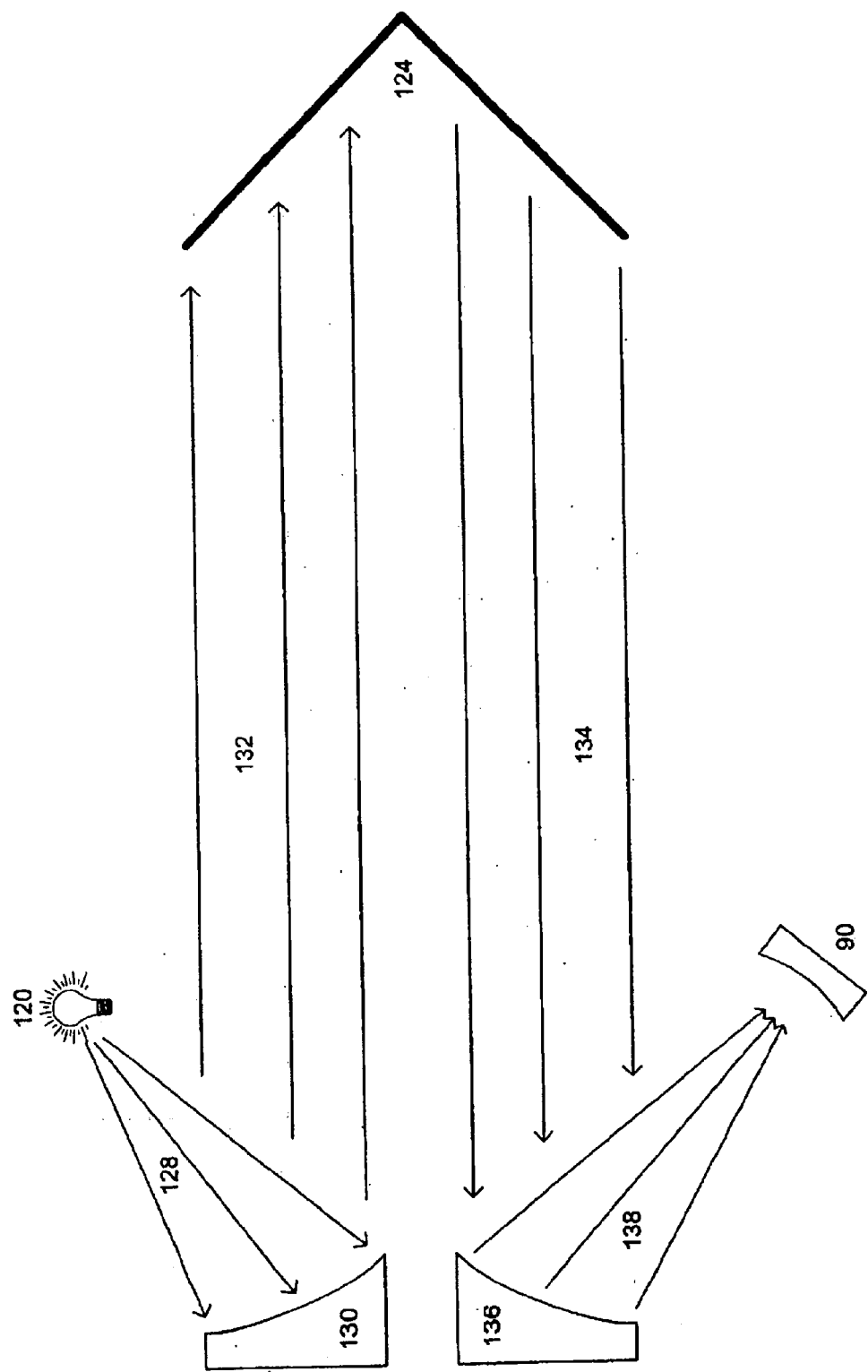
FIG. 10 illustrates the addition of reflectors to the components of FIG. 9.

Preferably, as illustrated in FIG. 10, the system also includes a first reflector 130 positioned to receive the beam 128 from the light source 120 and reflect the beam 132 toward the reflection unit 124. The reflection unit 124 is positioned to receive the beam 132 from the first reflector 130 and reflect the beam 134 toward a second reflector 136. Also preferably, the second reflector 136 is positioned to receive the beam 134 reflected by the refection unit 124 and reflect the beam 138 toward the detection unit 90. In a preferred embodiment, each reflector 130,136 comprises an off-axis paraboloidal mirror, however a spherical or other similar mirror could be used.

Figure 11:
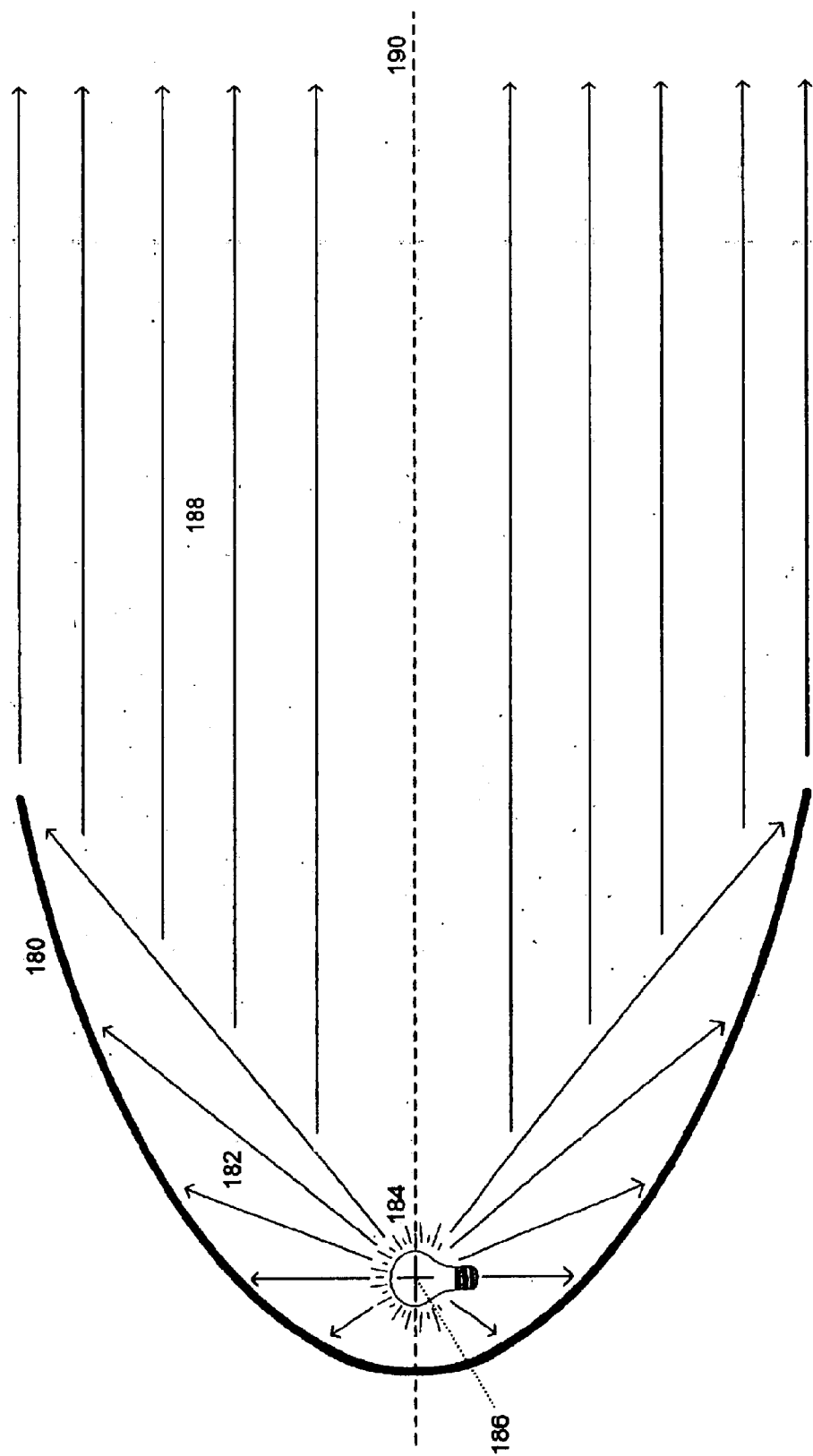
FIG. 11 illustrates the properties of a paraboloidal reflector.

Referring to FIG. 11, a paraboloidal mirror 180 has the property that light rays 182 emitted from and diverging from a small spot of a light source 184 placed near the paraboloidal mirror 180 focus 186 are reflected into a beam of rays 188 nearly parallel to the axis of rotation 190 of the mirror.

Figure 12:
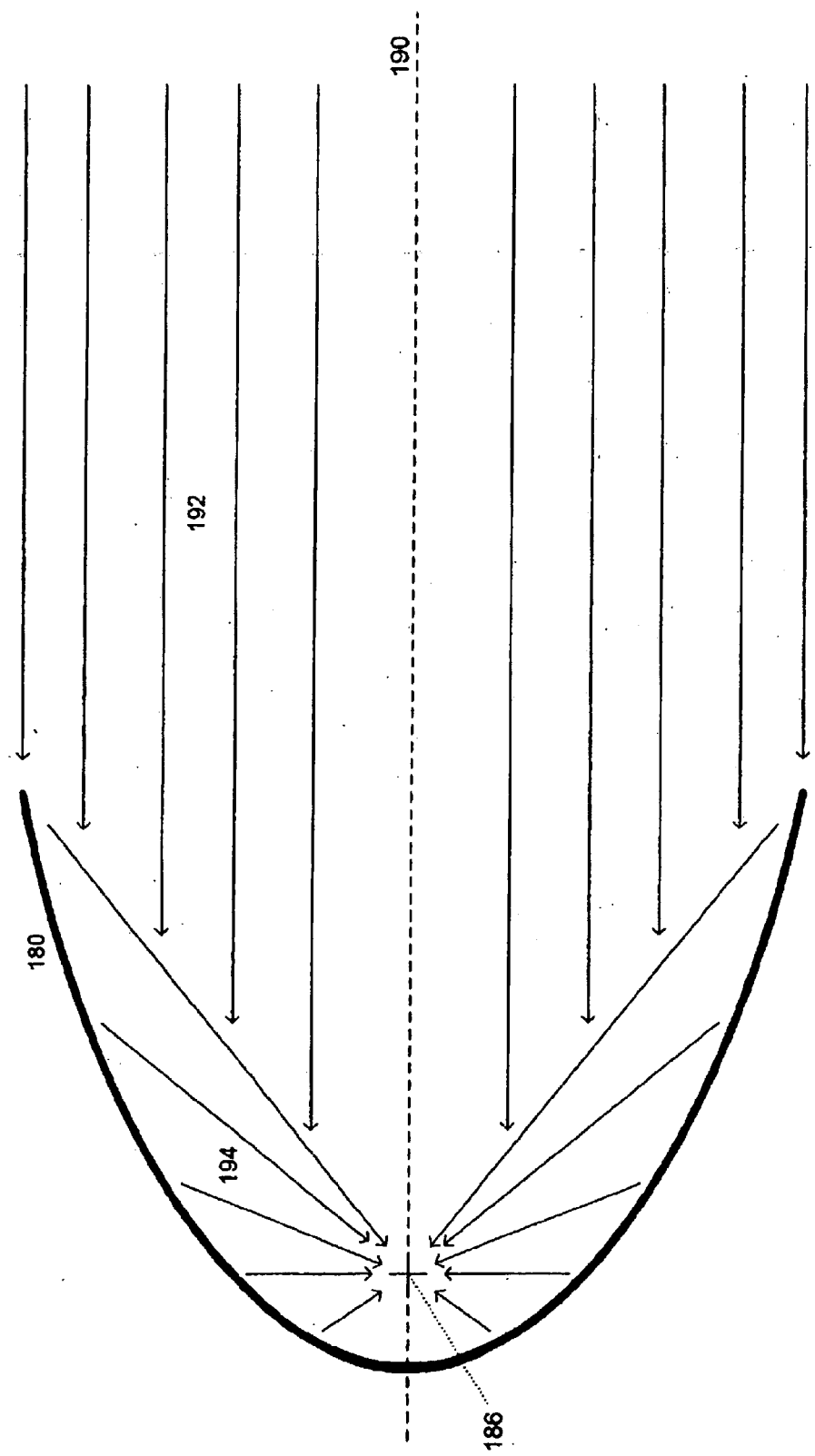
FIG. 12 further illustrates the properties of a paraboloidal reflector.

Conversely, as illustrated in FIG. 12, a beam of light rays 192 traveling nearly parallel to the axis of rotation 190 of a paraboloidal mirror 180 become rays 194 reflected toward and concentrated into a small spot near the paraboloidal mirror focus 186. The significance of a light beam of nearly parallel rays 192 is that the intensity of the light beam changes very little over a great distance, a desirable trait for long path, open-path gas detection systems. Off-axis paraboloidal mirrors have the advantage that the light source or detection unit may be located to the side of the reflected beam instead of in its midst. This means that the full diameter of the mirror can be used for the optical measurements. Layout of the source and detector components is also simplified. Spherical mirrors are more "fuzzy" at the focus if the spherical mirror is angled, the angle causing incoming/outgoing light rays to not be nearly as parallel as with the parallel rays 192 of the paraboloidal mirror 180. Light rays that do not travel in the parallel path are lost from the optical path and as a consequence, are part of the reduced efficiency of an optical system that utilizes spherical mirrors. Nonetheless, other factors such as availability of product, production cost, etc. all factor in the decision whether to use the preferred paraboloidal mirror 180 for sending/receiving light in the embodiment, or utilize spherical mirrors in their place.

Figure 13:
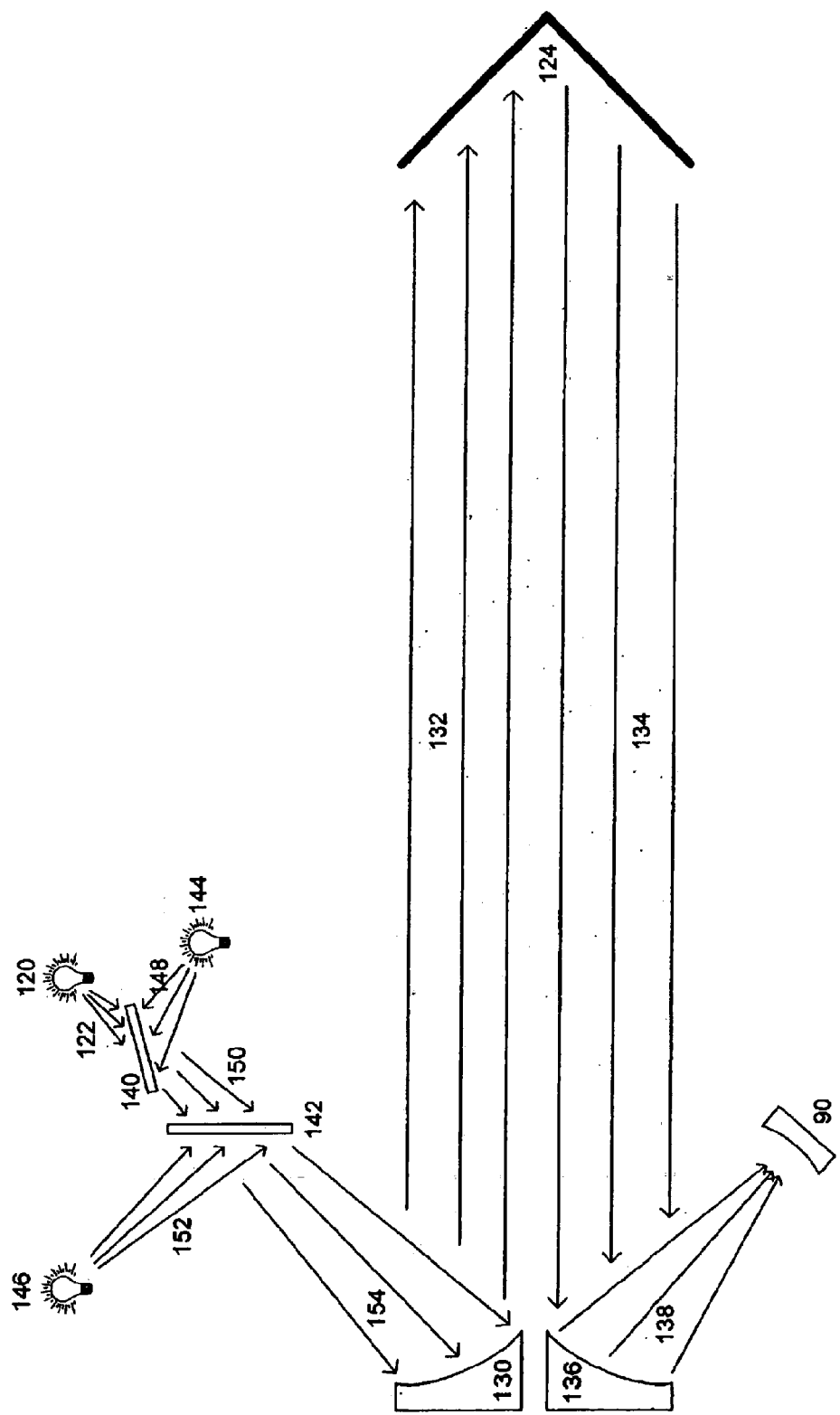
FIG. 13 illustrates the addition of multiple light sources with beam splitter/combiners to the components of FIG. 10.

Returning to FIG. 10, a beam of light travels along an optical path 128, 132, 134, and 138 from the light source 120, to the first reflector 130, to the reflection unit 124, to the second reflector 136, to the detection unit 90. In this embodiment, the system also includes, as seen in FIG. 13, one or more additional light sources 144,146, each capable of emitting a beam of light 148,152 having known emission intensities corresponding to one or more of infrared, visible, and ultraviolet spectra, as well as one or more beam splitter/combiners 140,142, if necessary, positioned to direct beams 148,152 from the additional light sources 144,146 along essentially the same optical path 154, 132, 134, and 138 as illustrated in FIG. 10. The beam splitter/combiners 140,142 may be neutral density filters, or alternatively they may be wavelength sensitive beam splitter/combiners, such as dichroic beam splitter/combiners.

Figure 14:
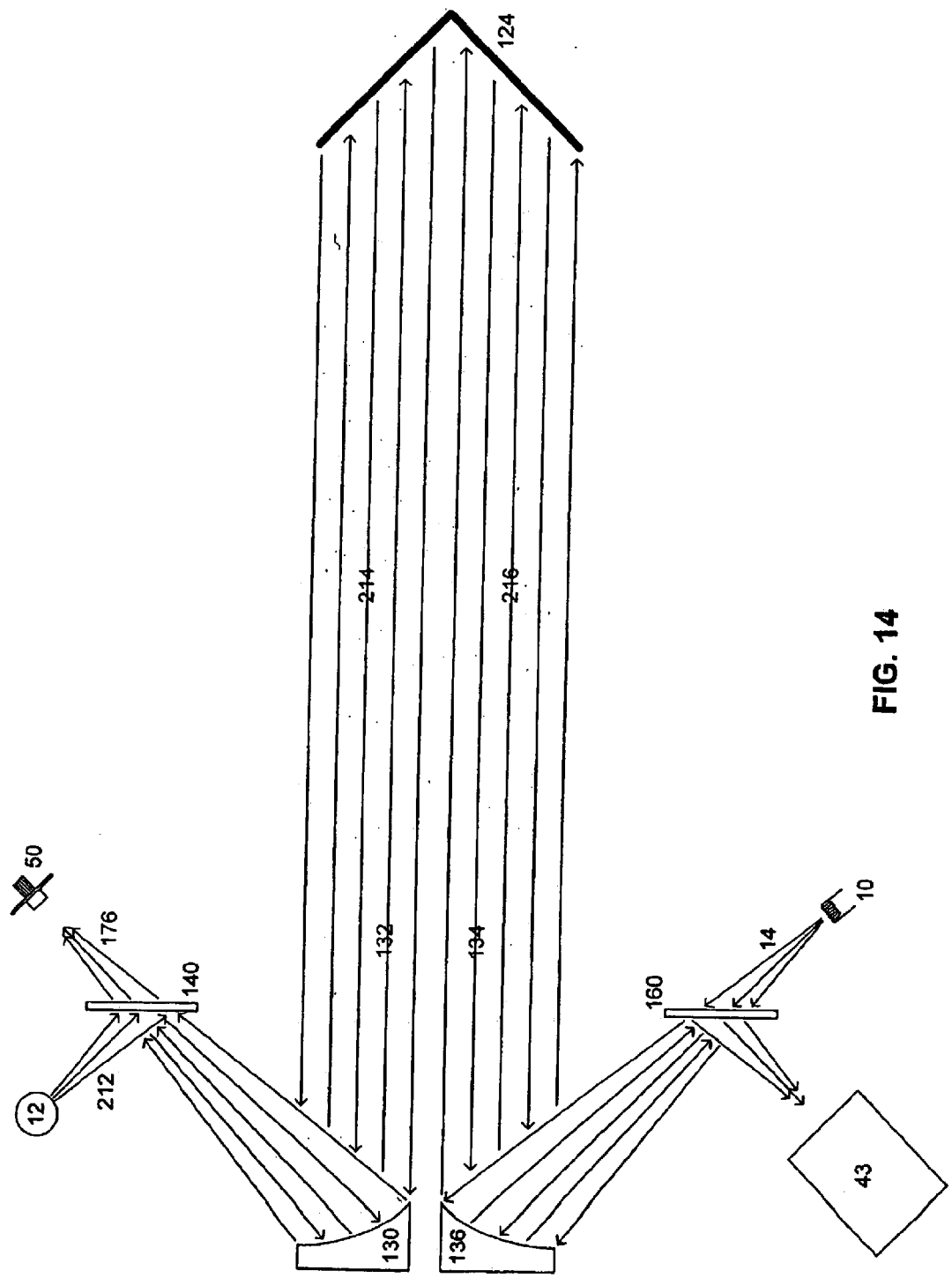
FIG. 14 illustrates a modification of the embodiment shown in FIG. 13 illustrating the arrangement of opposed sources.

In another embodiment, illustrated by FIG. 14, the light sources 10,12, beam splitter/combiners 140,160, infrared detector 50, and spectrometer 43 are positioned so that ultraviolet light beam 212 from source 12 is traveling along essentially the same optical path, but in the opposite direction from infrared light beam 14 from source 10. This innovation is referred to herein as "opposed sources". An embodiment using opposed sources may eliminate the need for additional expensive, light attenuating components. For instance, if ultraviolet light 212 is directed towards, instead of away from, the infrared detector 50, the signal from the infrared detector 50 can degrade. If light 212 from an ultraviolet source 12 is traveling in the opposite direction from the light 14 emanating from the infrared source 10, the ultraviolet light 212 is naturally kept away from the infrared detector 50 without the use of additional wavelength dependent filters or beam splitter/combiners. Light sources 12,10 and detectors 43, 50 need to be matched with optical components of corresponding F-numbers for efficient light transmission. An embodiment using opposed sources, and first and second reflectors 130,136 of significantly different F-number, allows the sources or detectors requiring a higher F-number to be matched with the reflector with the higher F-number, and the sources and detectors requiring a lower F-number to be matched with the reflector with the lower F-number. This eliminates the need for additional optical components for F-number matching. Finally, opposed sources may significantly simplify component layout and reduction of thermal and electrical interference among components.

FIG. 13 shows one possible arrangement of three sources 120, 144 and 146. In one preferred configuration, the source 120 is an infrared source, the source 144 is a visible light source, and source 146 is an ultraviolet light source. In this example, ultraviolet light reflects off splitter/combiner 142 but does not pass through any splitter/combiners. The infrared light passes through two splitter/combiners. However, the arrangement of these sources may be interchanged in any combination, and one or more source types may be omitted entirely.

FIG. 14 depicts an ultraviolet source 12 and an infrared source 10. The ultraviolet source 12 could also be combined with a visible light source in a manner similar to the combination shown in FIG. 1, either using a pass through ultraviolet source or by providing an additional splitter/combiner to combine the ultraviolet and visible light.

Thus, the many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

We claim:

1. A device for measuring particulate matter comprising:
a light source that emits light;
a receiver positioned to receive light emitted from said light source; and
a detection unit in communication with said receiver wherein said detection unit detects an amount of particulate matter based upon said light received by said receiver
wherein said detection unit determines the concentration of particulate matter using the relationship:

$$C = \frac{2 - \text{Log}_{10}\left(\frac{I_p}{I_o} \times 100\right)}{\varepsilon \times l}.$$

wherein $I_p$ is the amount of light after passing through the gas sample of interest;

$I_o$ is the amount of light that was originally sent through the entire sample path and not absorbed by the gas of interest;

$\varepsilon$ is the absorption coefficient for the gas of interest at a corresponding wavelength of absorption; and $l$ is the path length.

2. The device as recited in claim 1 wherein said light source emits light at wavelengths in the visible spectrum.

3. The device as recited in claim 1 wherein said light source emits light at al wavelength of 500 nanometers.

4. The device as recited in claim 1 wherein said detection unit determines the concentration of particulate matte by determining a concentration of particulate matter and scaling said concentration.

5. The device as recited in claim 1 further comprising a reflector positioned to receive said light emitted from said light source and to reflect said light to said receiver.

6. The device as recited in claim 1 further comprising:
a beam splitter/combiner positioned to receive light emitted from said light source; and
additional light sources positioned to emit light to said beam splitter/combiner so that the path of light emitted from said additional light sources follows the same optical path as said light emitted from said light source.

7. A method for determining a concentration of particulate matter comprising the steps of:
emitting light from a light source;
receiving said light emitted from said light source in a receiver;
determining an amount of particulate matte using said light received in said receiver;
wherein the step of determining an amount of particulate matter further comprises the step of suing the relationship:

$$C = \frac{2 - \text{Log}_{10}\left(\frac{I_p}{I_o} \times 100\right)}{\varepsilon \times l}.$$

wherein $I_p$ is the amount of light after passing through the gas sample of interest;

$I_o$ is the amount of light that was originally sent through the entire sample path and not absorbed by the gas of interest;

$\varepsilon$ is the absorption coefficient for the gas of interest at a corresponding wavelength of absorption; and $l$ is the path length.

8. The method as recited in claim 7 wherein said step of emitting light from said light source comprises the step of emitting light at wavelengths in the visible spectrum.

9. The method as recited in claim 7 wherein said step of emitting light from said light source comprises the step of emitting light at wavelength at 500 nanometers.

10. The method as recited in claim 7 further comprising the step of reflecting said light emitted from said light source to said receiver.

11. The method as recited in claim 7 further comprising the step of reflecting said light emitted from said light source to said receiver.

12. A system for measuring particulate matter comprising:
a light source means for emitting light;
a receiver means for receiving said light emitted from said light source means, said receiver means positioned to receive said light emitted from said light source means; and
a detection unit means for determining an amount of particulate matter based upon the light received by said receiver, said detection unit means in communication with said receiver means;

wherein said detection unit means determines the concentration of particulate matter using the relationship:

$$C = \frac{2 - \text{Log}_{10}\left(\frac{I_p}{I_o} \times 100\right)}{\varepsilon \times l}$$

wherein $I_p$ is the amount of light after passing through the gas sample of interest;

$I_o$ is the amount of light that was originally sent through the entire sample path and not absorbed by the gas of interest;

$\varepsilon$ is the absorption coefficient for the gas of interest at a corresponding wavelength of absorption; and l is the path length.

13. The system as recited in claim 12 wherein said light source means emits light at wavelengths in the visible spectrum.

14. The system as recited in claim 12 wherein said light source means emits light at a wavelength of 500 nanometers.

15. The system as recited in claim 12 wherein said detection unit means determines the concentration of particulate matter by determining a concentration of particulate matter and scaling said concentration.

16. The system as recited in claim 12 further comprising a reflector means fro reflecting said light emitted from said light source means to said receiver means.

17. The system as recited in claim 12 further comprising:

a beam splitter/combiner means for receiving light emitted from said light source means; and an additional light source means for emitting light to said beam splitter/combiner means so that the path of light emitted from said additional light source means follows the same optical path as said light emitted from said light source means.

* * * * *

UNITED STATES PATENT AND TRADEMARK OFFICE
CERTIFICATE OF CORRECTION

PATENT NO. : 6,900,893 B2
DATED : May 31, 2005
INVENTOR(S) : Theresa A. Foley et al.

It is certified that error appears in the above-identified patent and that said Letters Patent is hereby corrected as shown below:

Title page,
Item [56], References cited, OTHER PUBLICATIONS please add:
-- Bureau of Automotive Repair; "On Road Emissions Measurement System (OREMS) Specifications"; OREMS Specifications-Version O, Jan. 28, 2002; 2002 California DCA/ BAR;
JIMÉNEZ-PALACIOS, José Luis; "Understanding and Quantifying Motor Vehicle Emissions with Vehicle Specific Power and TILDAS Remote Sensing"; Massachusetts Institute of Technology, Feb. 1999. --.

Column 19,
Line 67, please delete "al" and insert -- a --;

Column 20,
Lines 2 and 20, please delete "matte" and replace with -- matter --;
Line 23, please delete "suing" and replace with -- using --;
Line 34, please delete the space after "wherein" so the sentence reads as -- wherein $I_p$ is the amount of light after passing through the gas sample of interest --;
Line 49, please insert -- a -- after "at" and replace "wavelength at" with -- wavelength of --;

Column 21,
Line 9, please delete the space after "wherein" so the sentence reads as -- wherein $I_p$ is the amount of light after passing through the gas sample of interest --.

Column 22,
Line 8, please delete "fro" and replace with -- for --.

Signed and Sealed this

Thirteenth Day of September, 2005

JON W. DUDAS
*Director of the United States Patent and Trademark Office*